(12) United States Patent
Matsunobu et al.

(10) Patent No.: US 10,842,367 B2
(45) Date of Patent: Nov. 24, 2020

(54) ILLUMINATION APPARATUS, METHOD AND MEDICAL IMAGING SYSTEM

(71) Applicant: Sony Corporation, Tokyo (JP)

(72) Inventors: Goh Matsunobu, Kanagawa (JP); Takashi Yamaguchi, Kanagawa (JP); Akio Furukawa, Tokyo (JP)

(73) Assignee: Sony Corporation, Tokyo (JP)

( * ) Notice: Subject to any disclaimer, the term of this patent is extended or adjusted under 35 U.S.C. 154(b) by 707 days.

(21) Appl. No.: 15/313,603

(22) PCT Filed: Mar. 25, 2015

(86) PCT No.: PCT/JP2015/001705
§ 371 (c)(1),
(2) Date: Nov. 23, 2016

(87) PCT Pub. No.: WO2015/182025
PCT Pub. Date: Dec. 3, 2015

(65) Prior Publication Data
US 2017/0209032 A1 Jul. 27, 2017

(30) Foreign Application Priority Data

May 30, 2014 (JP) ................................. 2014-111994
May 30, 2014 (JP) ................................. 2014-111995

(51) Int. Cl.
*F21S 4/00* (2016.01)
*A61B 1/07* (2006.01)
(Continued)

(52) U.S. Cl.
CPC ............ *A61B 1/07* (2013.01); *A61B 1/00167* (2013.01); *A61B 1/0638* (2013.01);
(Continued)

(58) Field of Classification Search
CPC ........ A61B 1/07; A61B 1/0669; A61B 1/0638; A61B 1/00167; G02B 27/30;
(Continued)

(56) References Cited

U.S. PATENT DOCUMENTS

| | | | |
|---|---|---|---|
| 2007/0201788 A1* | 8/2007 | Liu ...................... | A61B 5/0059 385/12 |
| 2009/0009759 A1* | 1/2009 | Backman ............ | A61B 5/0084 356/303 |

(Continued)

FOREIGN PATENT DOCUMENTS

| | | |
|---|---|---|
| CN | 101099104 A | 1/2008 |
| CN | 102499615 A | 6/2012 |

(Continued)

OTHER PUBLICATIONS

Japanese Office Action dated Jan. 16, 2018 in connection with Japanese Application No. 2014-111994. English translation.

(Continued)

*Primary Examiner* — Ali Alavi
(74) *Attorney, Agent, or Firm* — Wolf, Greenfield & Sacks, P.C.

(57) ABSTRACT

An illumination apparatus includes an optical apparatus configured to optically process laser light to produce illumination light such that speckle noise in the illumination light is reduced. The optical apparatus includes at least one collimator (130) configured to collimate the laser light and a diffuser (140) configured to diffuse the laser light.

29 Claims, 25 Drawing Sheets

(51) Int. Cl.
*A61B 1/00* (2006.01)
*A61B 1/06* (2006.01)
*G02B 27/48* (2006.01)
*G02B 23/24* (2006.01)
*G02B 27/14* (2006.01)
*G02B 6/42* (2006.01)
*G02B 6/00* (2006.01)
*F21V 8/00* (2006.01)
*G02B 6/32* (2006.01)
*G02B 27/10* (2006.01)
*G02B 27/30* (2006.01)

(52) U.S. Cl.
CPC ............ *A61B 1/0669* (2013.01); *G02B 6/00* (2013.01); *G02B 6/0008* (2013.01); *G02B 6/32* (2013.01); *G02B 6/42* (2013.01); *G02B 23/2469* (2013.01); *G02B 27/1006* (2013.01); *G02B 27/141* (2013.01); *G02B 27/30* (2013.01); *G02B 27/48* (2013.01)

(58) Field of Classification Search
CPC .... G02B 27/006; G02B 27/141; G02B 27/48; G02B 6/32; G02B 6/0008; G02B 6/00; G02B 6/42; G02B 23/2409
USPC .......................................................... 362/572
See application file for complete search history.

(56) References Cited

U.S. PATENT DOCUMENTS

| | | | | |
|---|---|---|---|---|
| 2010/0253769 | A1* | 10/2010 | Coppeta | ............. G02B 27/1026 248/346.01 |
| 2011/0037953 | A1 | 2/2011 | Nizani et al. | |
| 2012/0307512 | A1* | 12/2012 | Cogger | .................. G02B 21/06 362/553 |
| 2014/0300873 | A1 | 10/2014 | Miyamoto et al. | |

FOREIGN PATENT DOCUMENTS

| | | |
|---|---|---|
| DE | 10 2009 005839 A1 | 7/2010 |
| EP | 1825317 | 8/2007 |
| EP | 2 793 077 A1 | 10/2014 |
| JP | 03-155518 A | 7/1991 |
| JP | 2003-156710 A | 5/2003 |
| JP | 2008-043493 A | 2/2008 |
| JP | 2009-198736 A | 9/2009 |
| JP | 2009-240560 A | 10/2009 |
| JP | 2010-042153 A | 2/2010 |
| JP | 2010-172651 A | 8/2010 |
| JP | 2010-175549 A | 8/2010 |
| JP | 2010-175579 A | 8/2010 |
| JP | 2012-005785 A | 1/2012 |
| JP | 2012-231835 A | 11/2012 |
| JP | 2012-248401 A | 12/2012 |
| JP | 2013-090706 A | 5/2013 |
| JP | 2013-099458 A | 5/2013 |
| JP | 2013-195489 A | 9/2013 |
| JP | 2014-007057 A | 1/2014 |
| WO | WO 2006/057768 A2 | 6/2006 |
| WO | WO 2013/088466 A1 | 6/2013 |
| WO | WO 2013/146014 A1 | 10/2013 |

OTHER PUBLICATIONS

Japanese Office Action dated Jan. 23, 2018 in connection with Japanese Application No. 2014-111995. English translation.
International Preliminary Report on Patentability dated Dec. 15, 2016 in connection with International Application No. PCT/JP2015/001705.
European Communication Pursuant to Article 94(3) EPC dated Jun. 22, 2018 in connection with European Application No. 15 716 880.8.
Chinese Office Action dated Sep. 4, 2018 in connection with Chinese Application 201580268018, and English translation thereof.
European Communication pursuant to Article 94(3) dated Feb. 1, 2019 in connection with European Application No. 15 716 880.8.
International Search Report and Written Opinion dated Jun. 1, 2015 in connection with International Application No. PCT/JP2015/001705.
Japanese Office Action dated Jul. 9, 2019 in connection with Japanese Application No. 2018-158997, and English translation thereof.

* cited by examiner

[Fig. 1A]
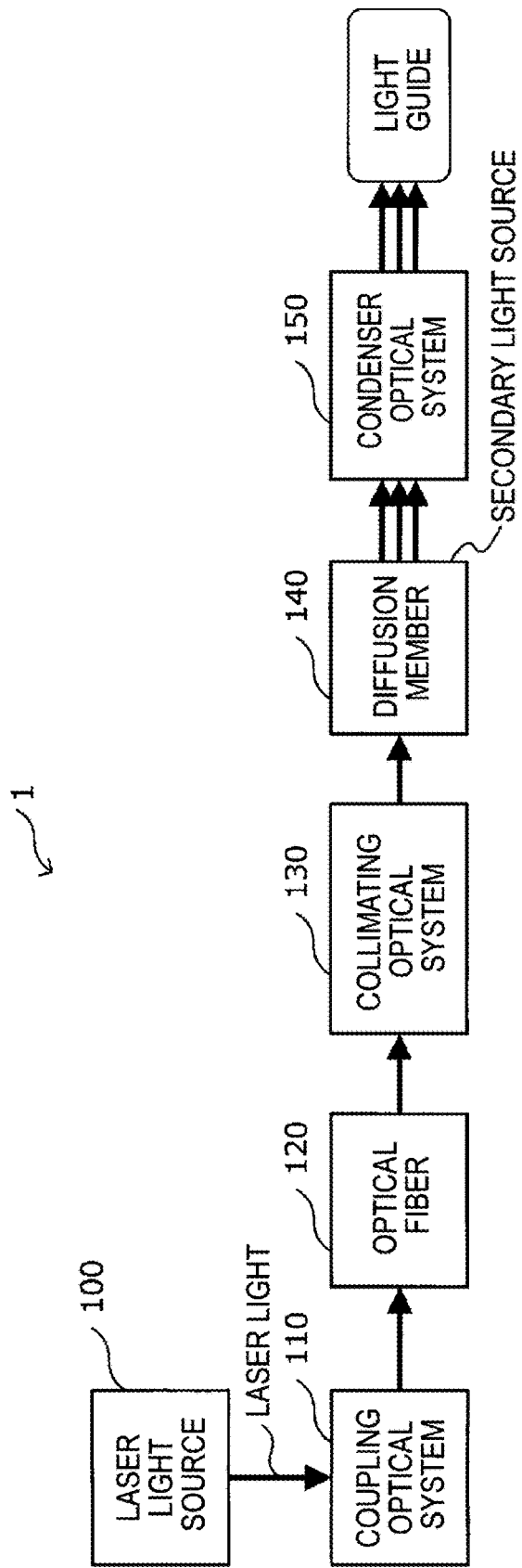

[Fig. 1B]
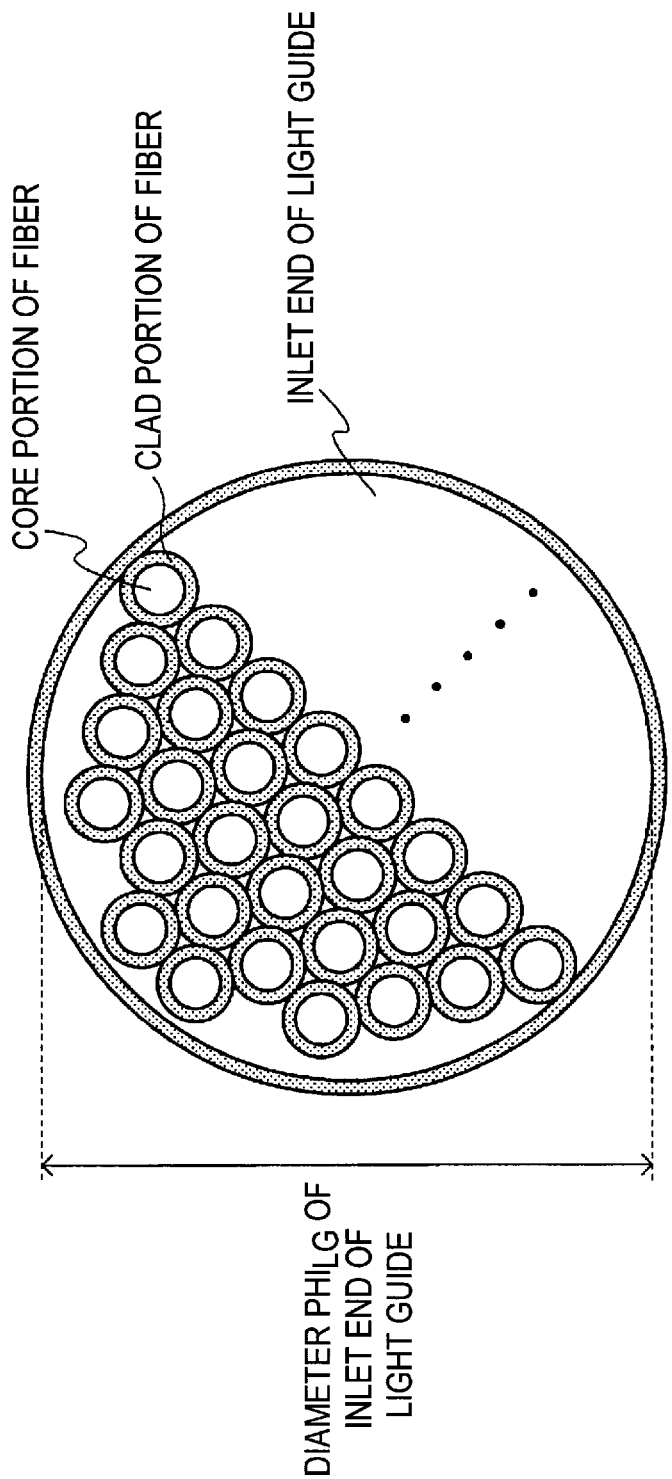

[Fig. 2]
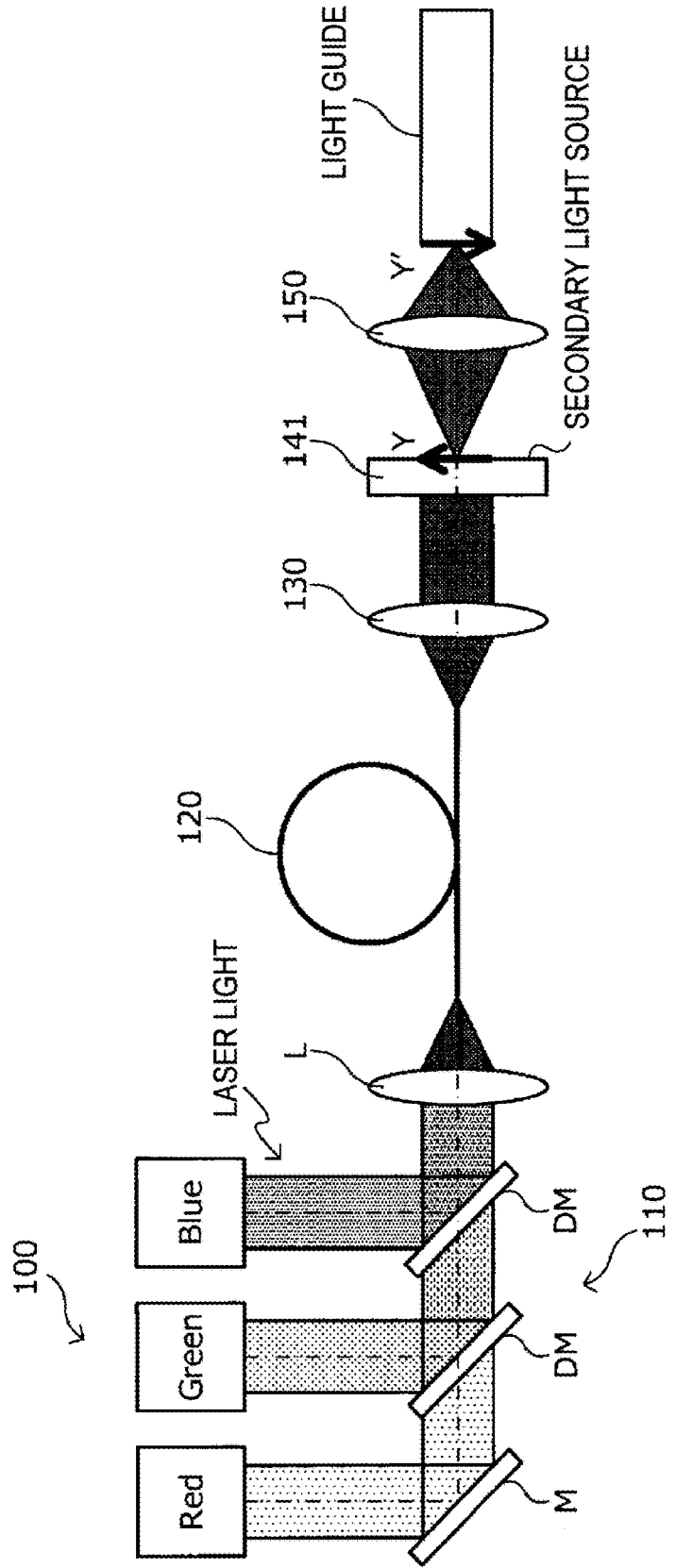

[Fig. 3]
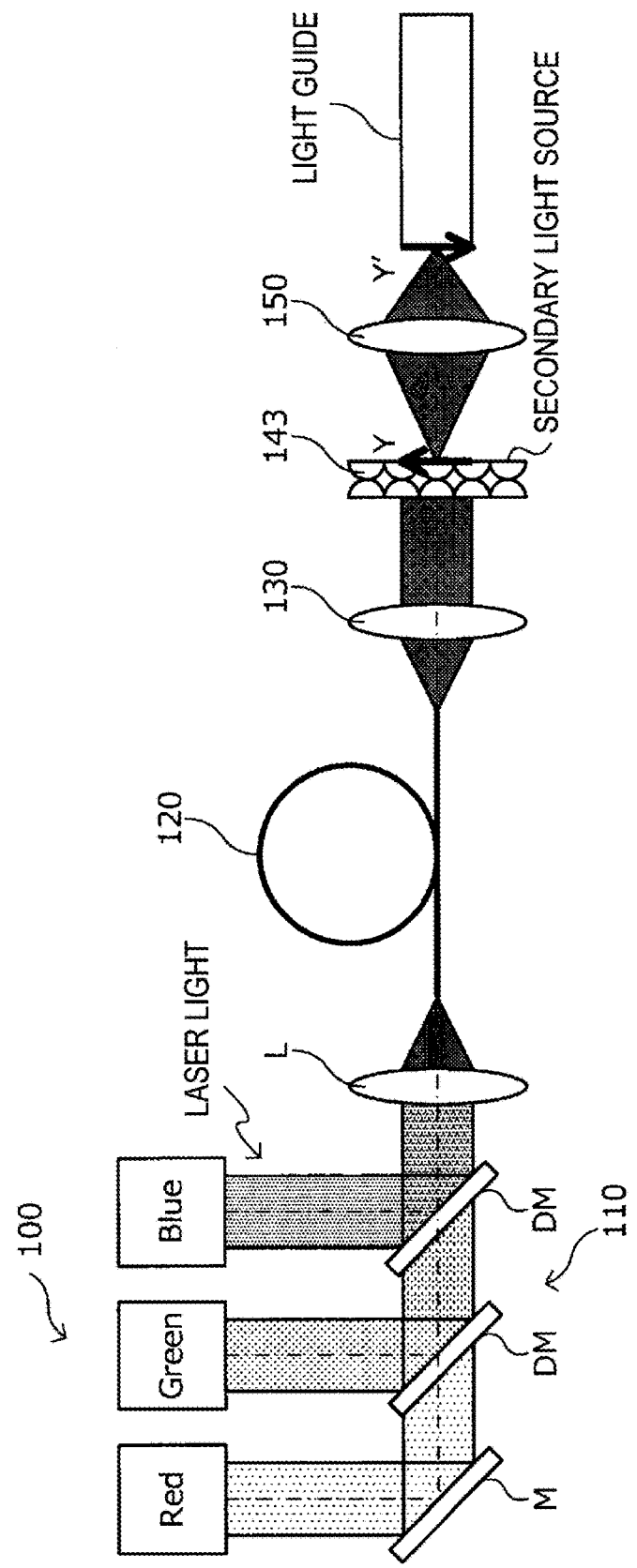

[Fig. 4]
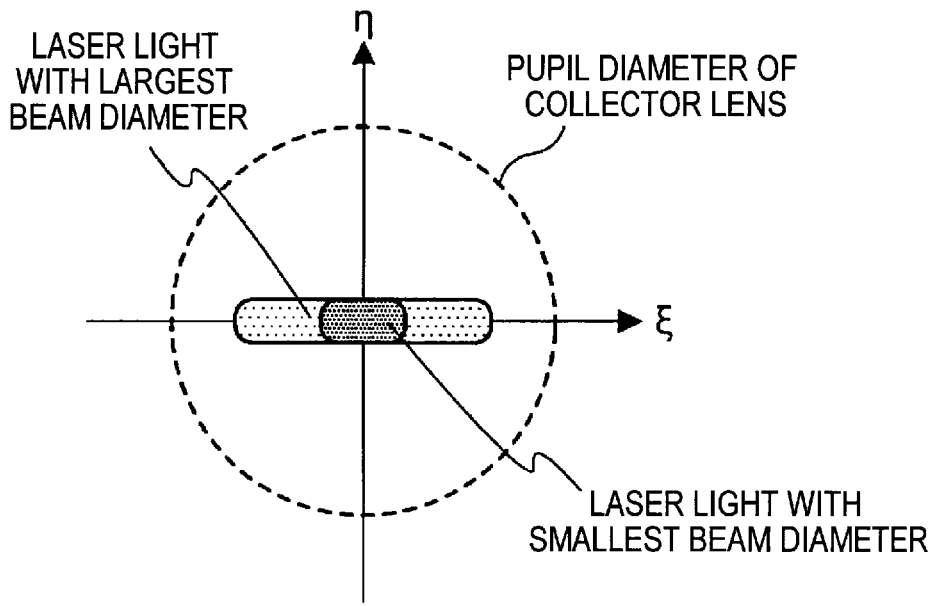
[Fig. 5]
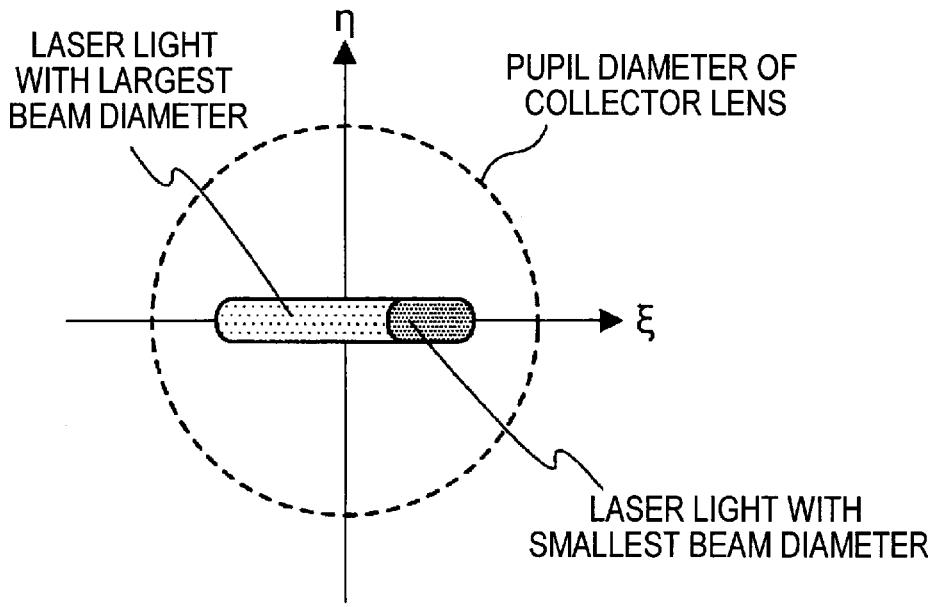

[Fig. 6]
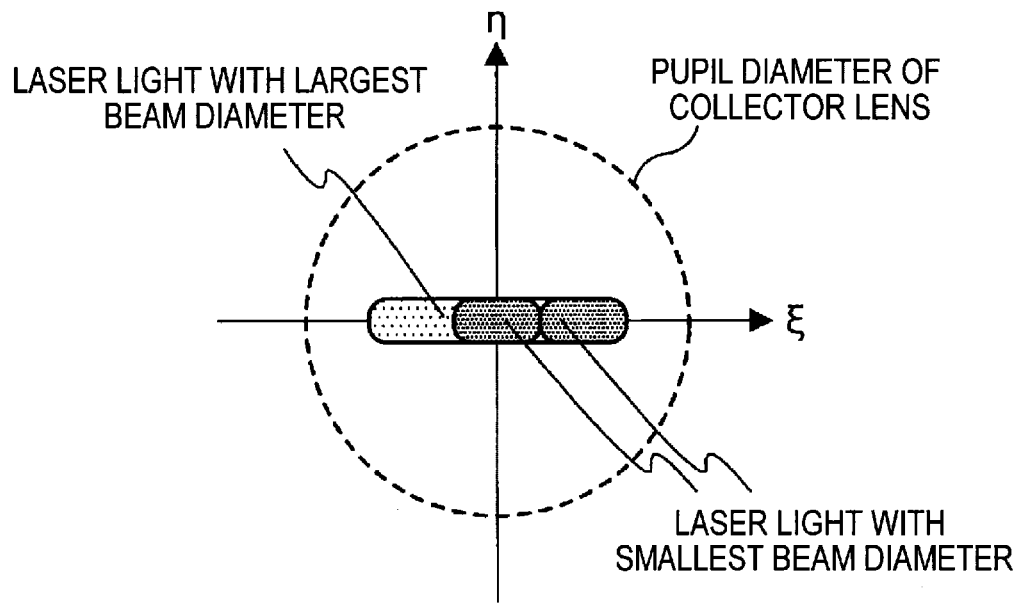
[Fig. 7]
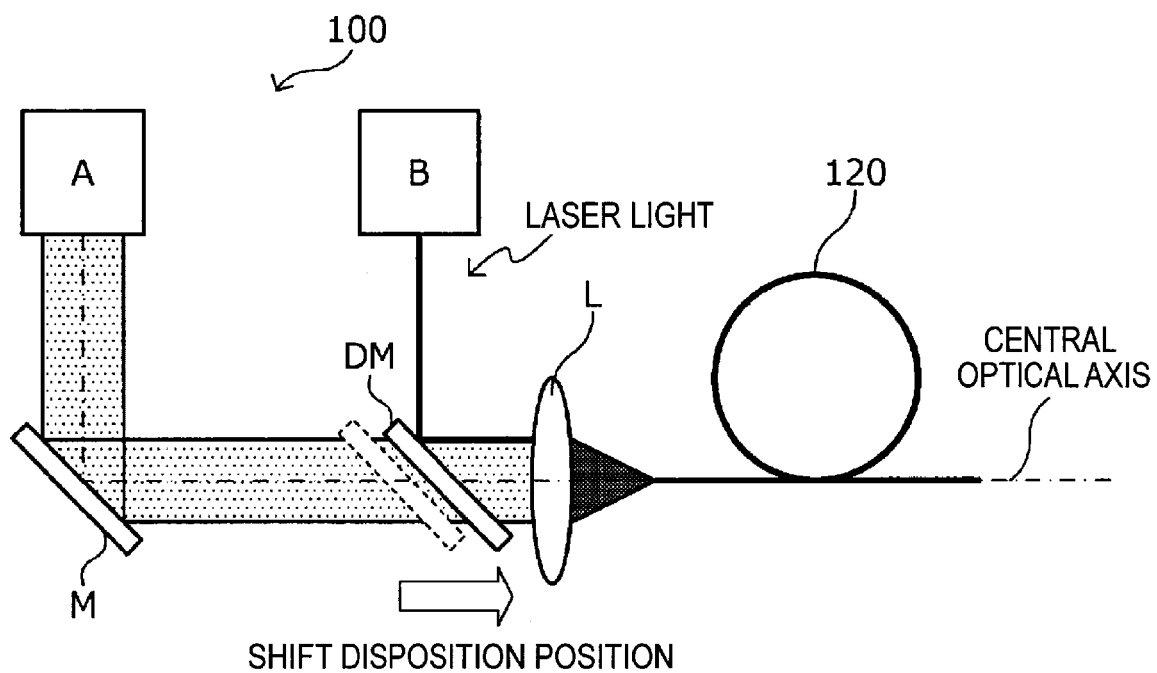

[Fig. 8]
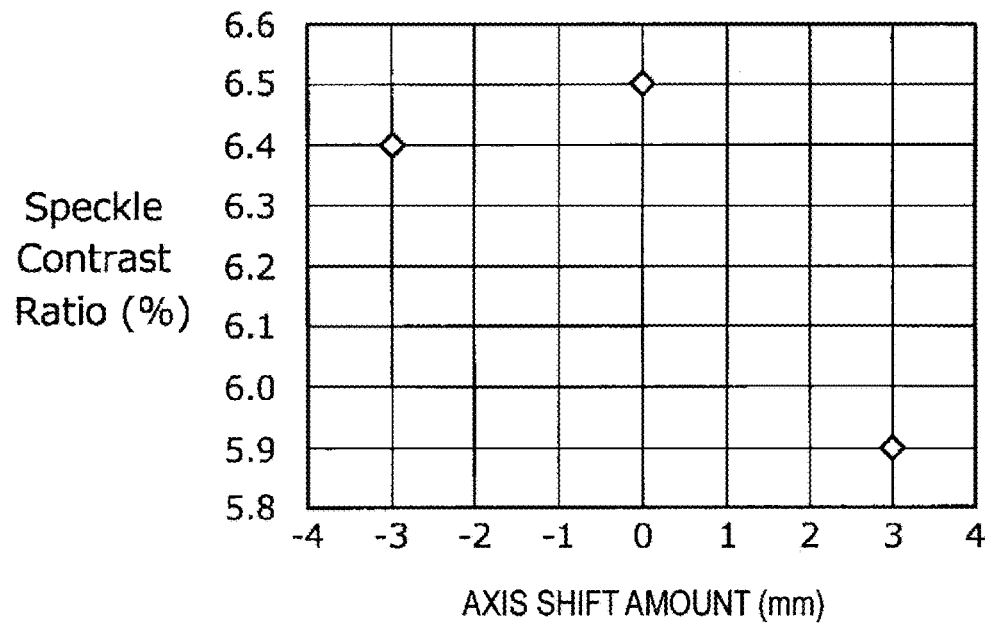
[Fig. 9A]
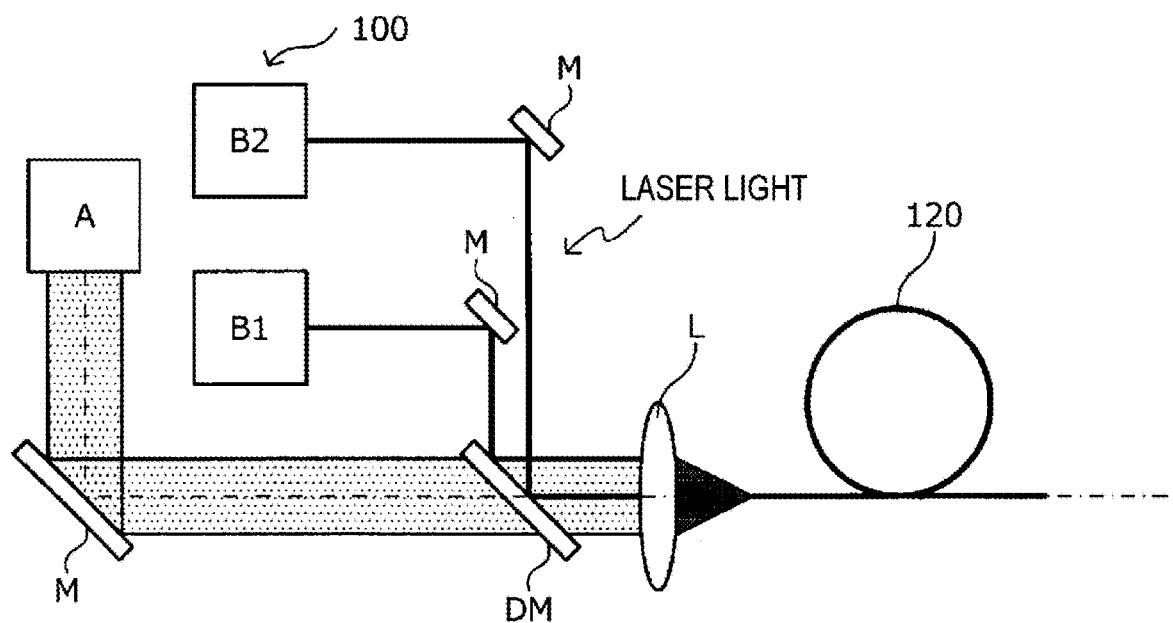

[Fig. 9B]
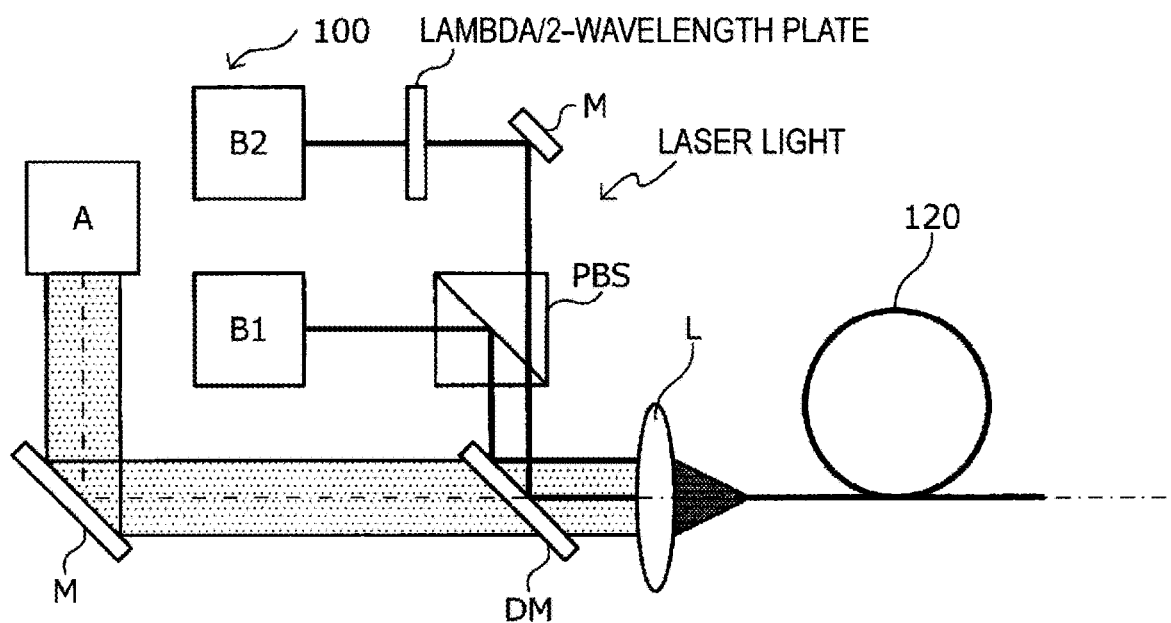
[Fig. 10]
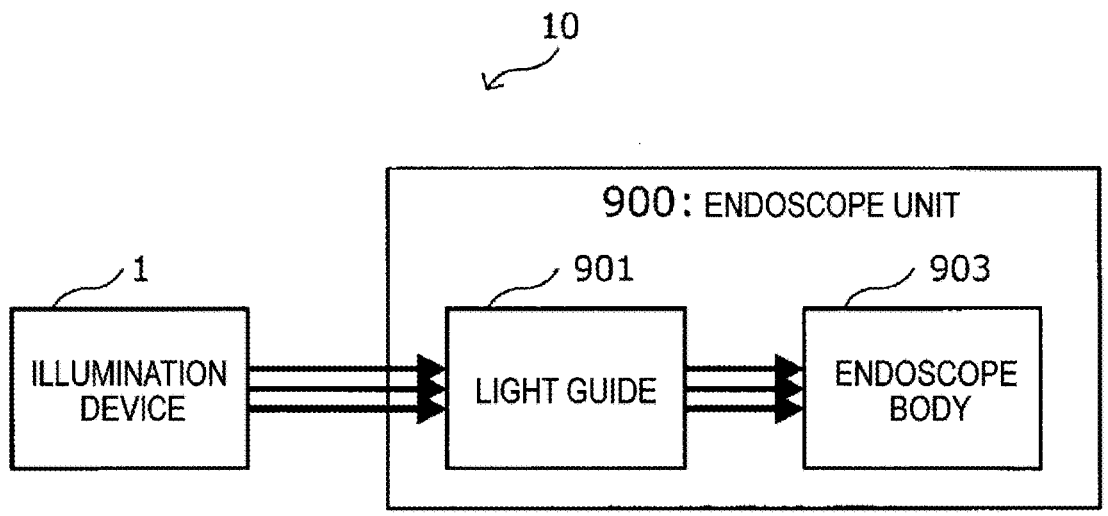

[Fig. 11]
|   | A | B | C |
|---|---|---|---|
| f | 11.727 | 11.727 | 11.727 |
| S1 to H | 10.773 | 10.773 | 10.773 |
| β | 0.4 | 0.6 | 1.2 |
| OBJ | 30.273 | 20.500 | 10.728 |
| X | 29.319 | 19.546 | 9.773 |
| SURFACE NUMBER S | RADIUS OF CURVATURE r | CENTRAL THICKNESS INTERVAL d | REFRACTIVE INDEX n | ABBE NUMBER ν |
|---|---|---|---|---|
| 1 | ∞ | 5.9 | 1.51680 | 64.2 |
| 2 | -31.525 | 0.2 | | |
| 3 | 46.816 | 6.4 | 1.51680 | 64.2 |
| 4 | -60.149 | 0.2 | | |
| 5 | 26.357 | 6.8 | 1.51680 | 64.2 |
| 6 | ∞ | 0.2 | | |
| 7* | 9.937 | 13 | 1.52301 | 58.6 |
| 8 | ∞ | | | |
\* : ROTATIONALLY SYMMETRIC ASPHERIC SURFACE
ASPHERIC SURFACE DATA: $K = -0.776872$, $A4 = 0.187240 \times 10^{-4}$
[Fig. 12A]
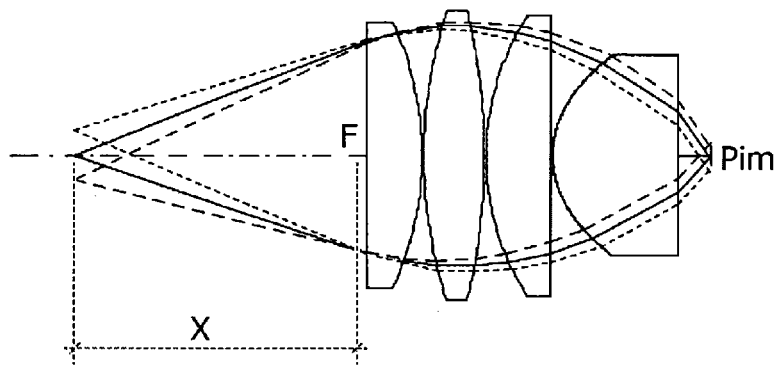

[Fig. 12B]
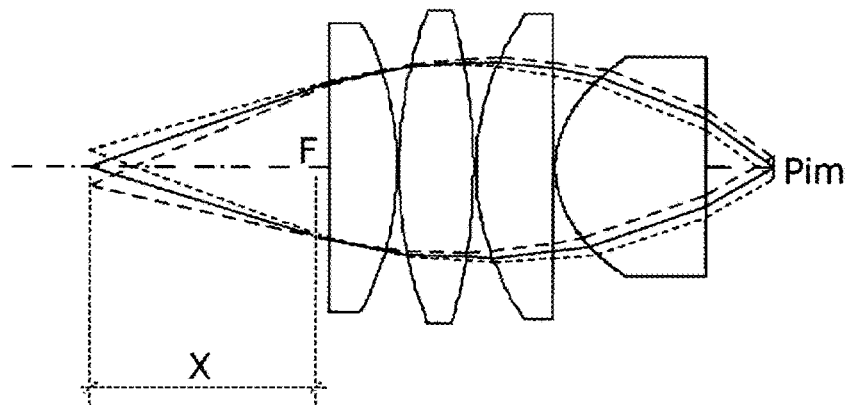
[Fig. 12C]
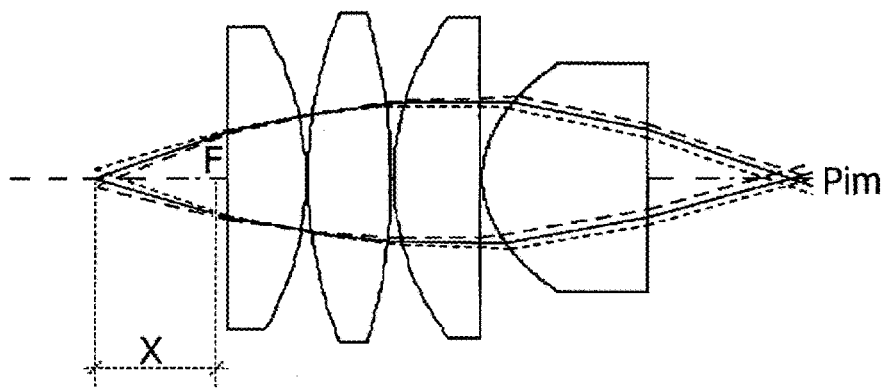
[Fig. 13A]
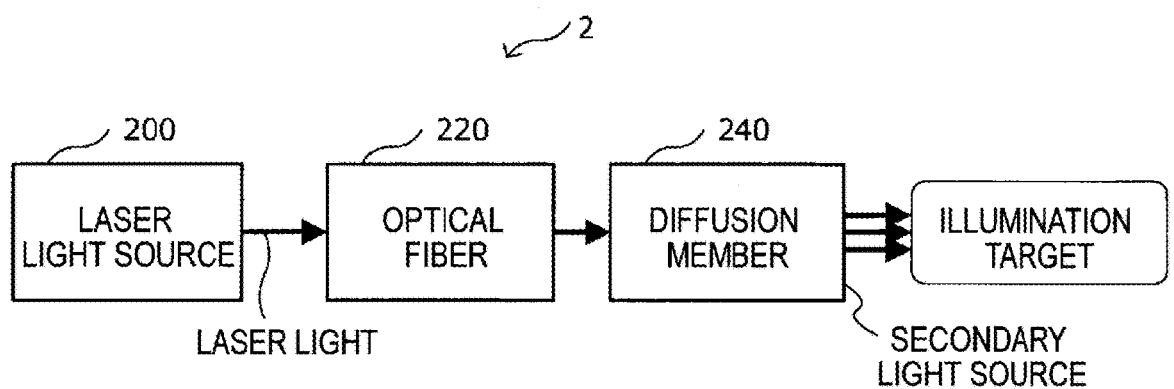

[Fig. 13B]
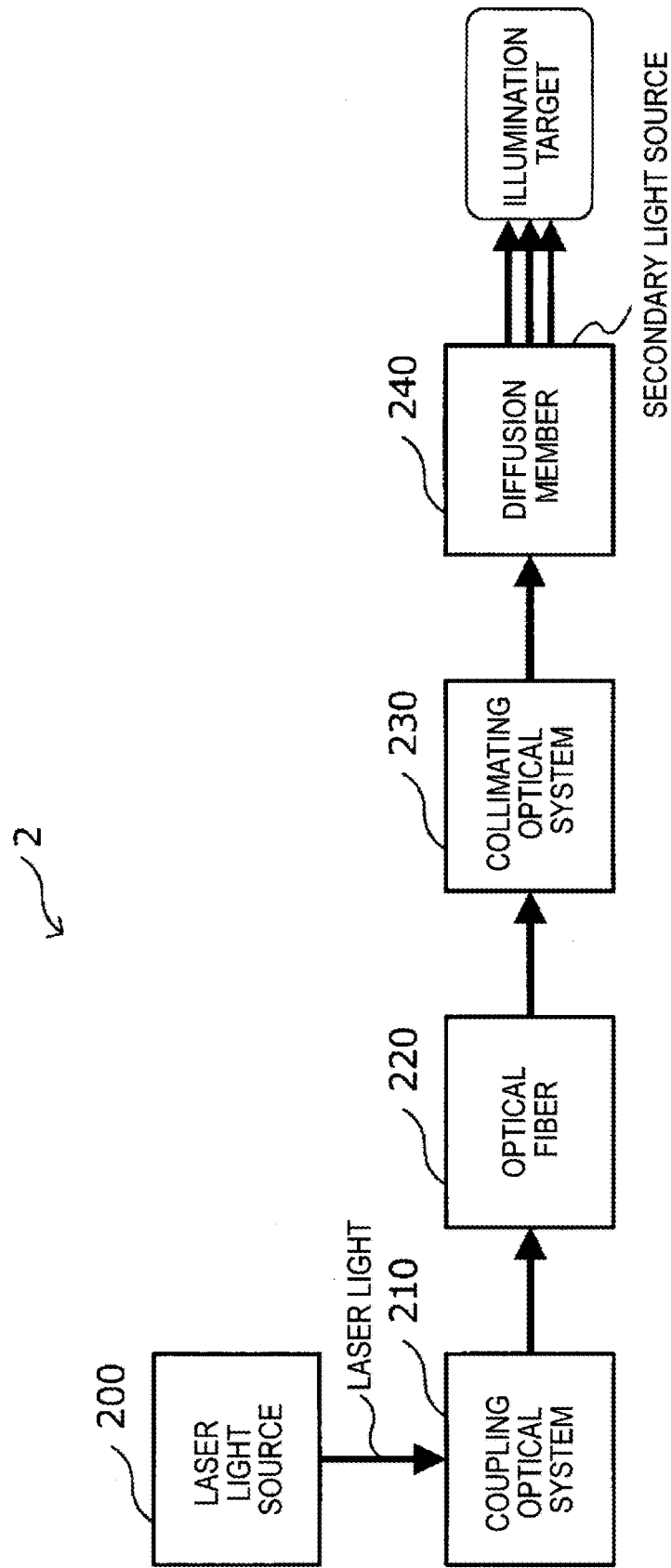

[Fig. 14A]
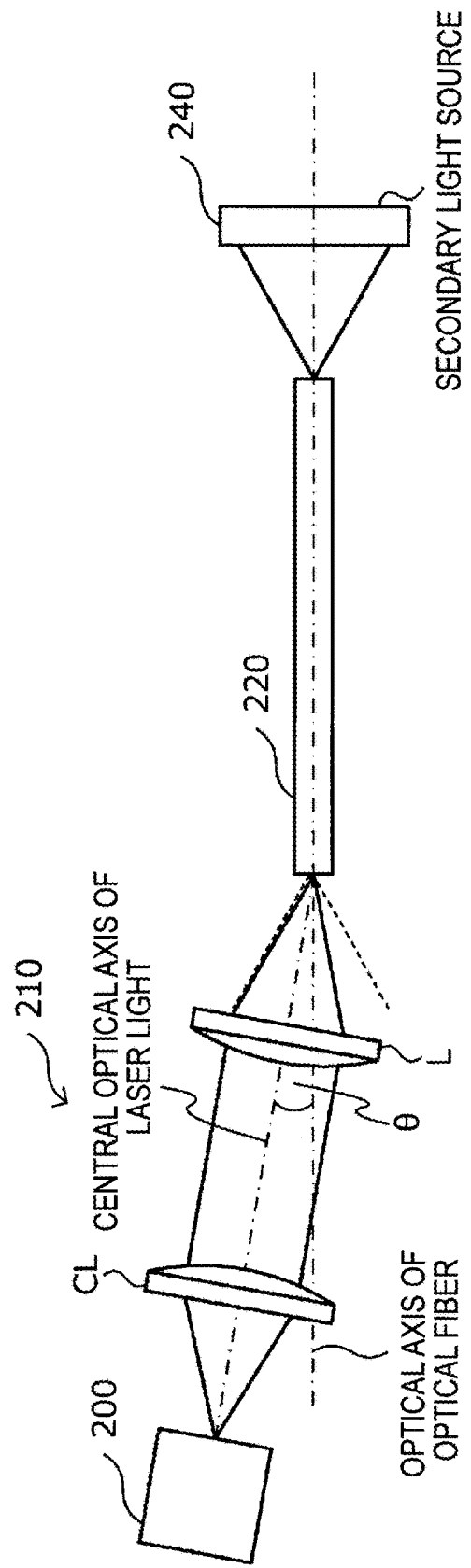

[Fig. 14B]
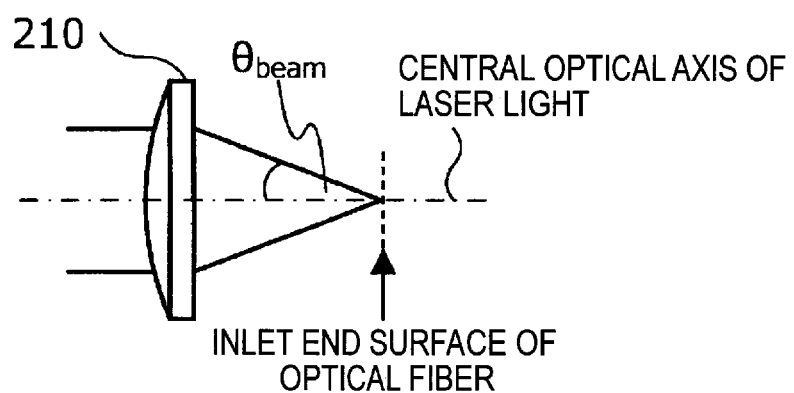
[Fig. 14C]
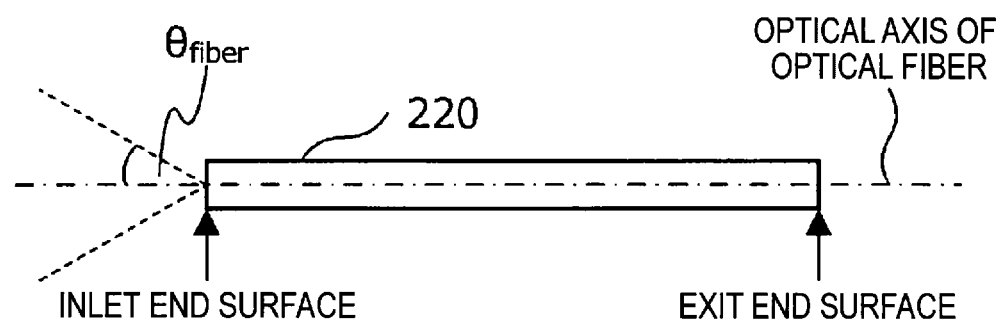

[Fig. 15]
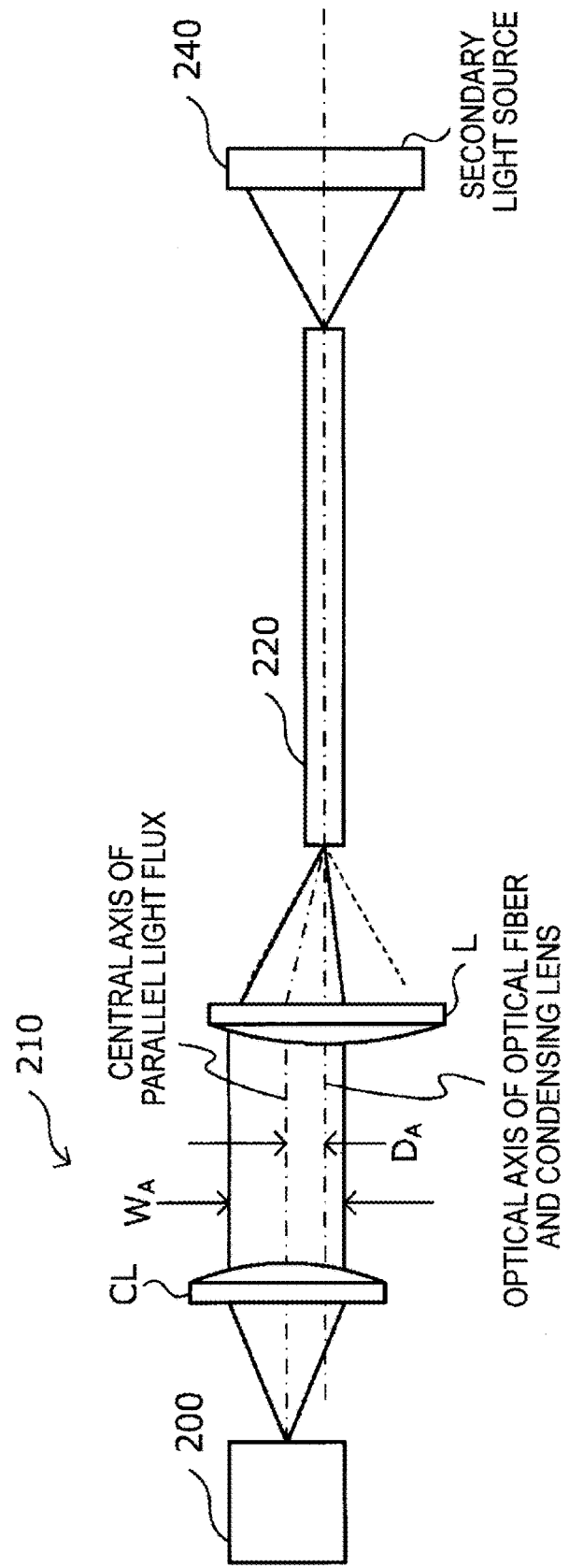

[Fig. 16]
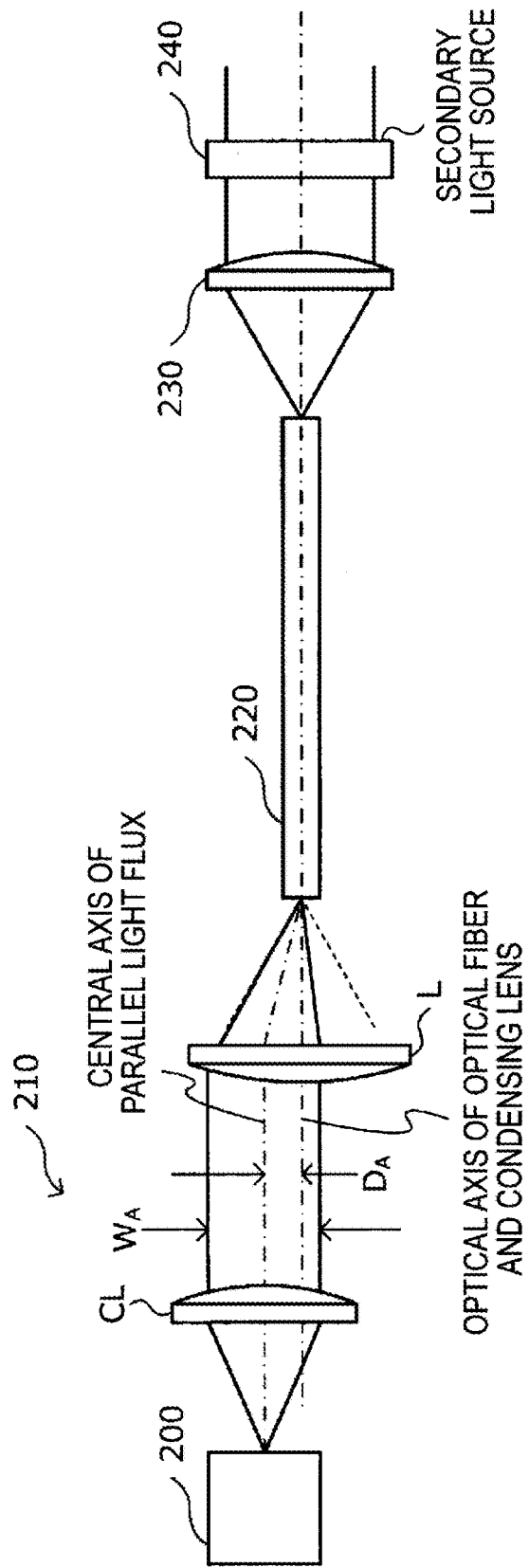

[Fig. 17]
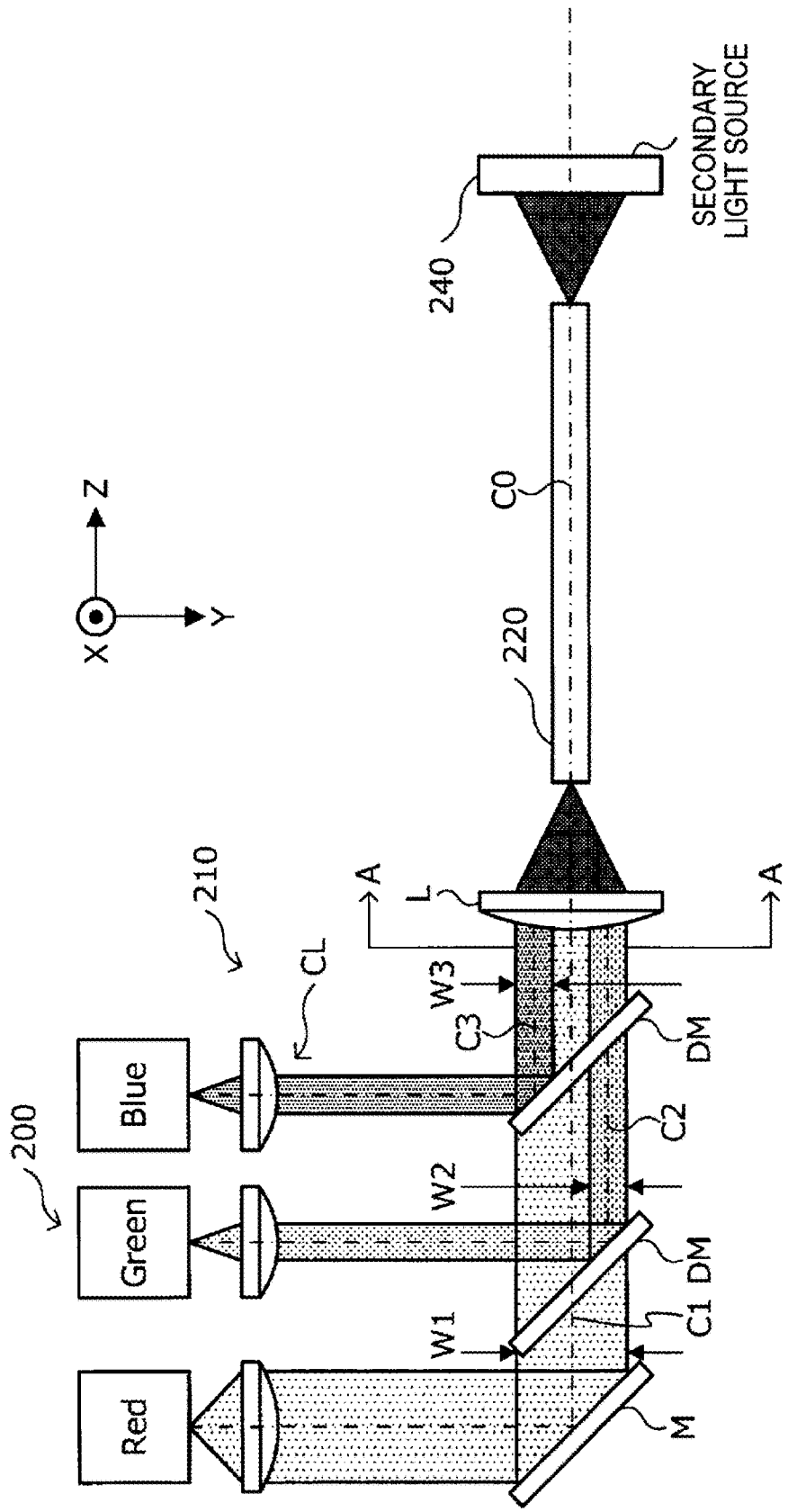

[Fig. 18A]
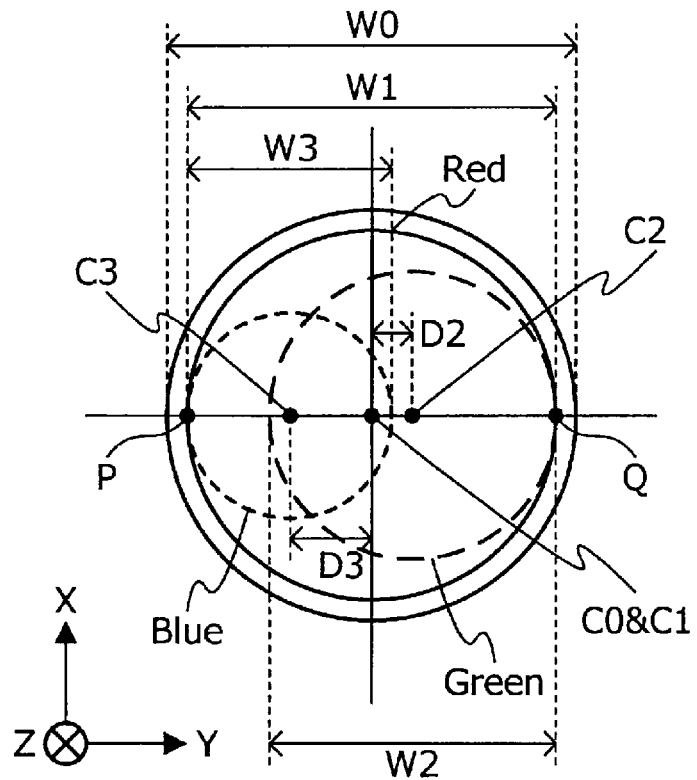
[Fig. 18B]
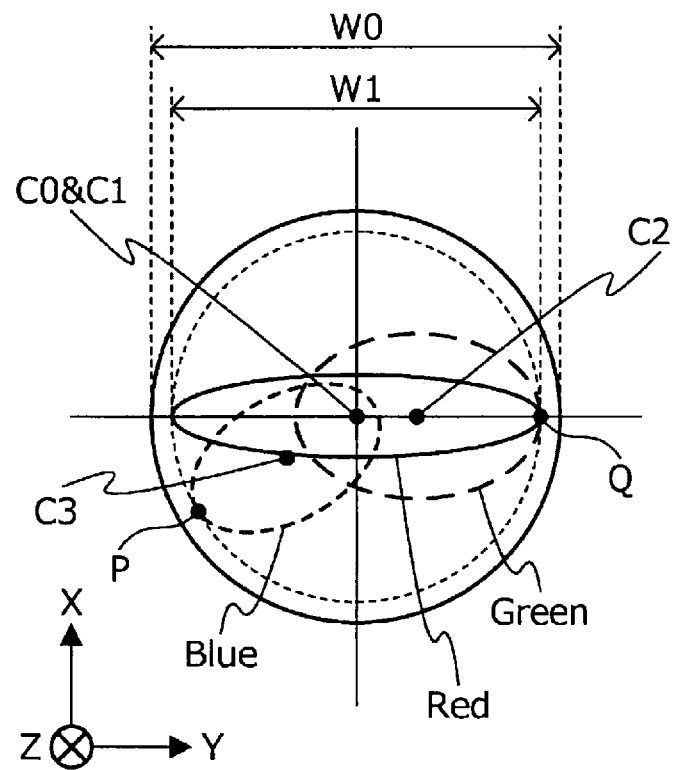

[Fig. 19]
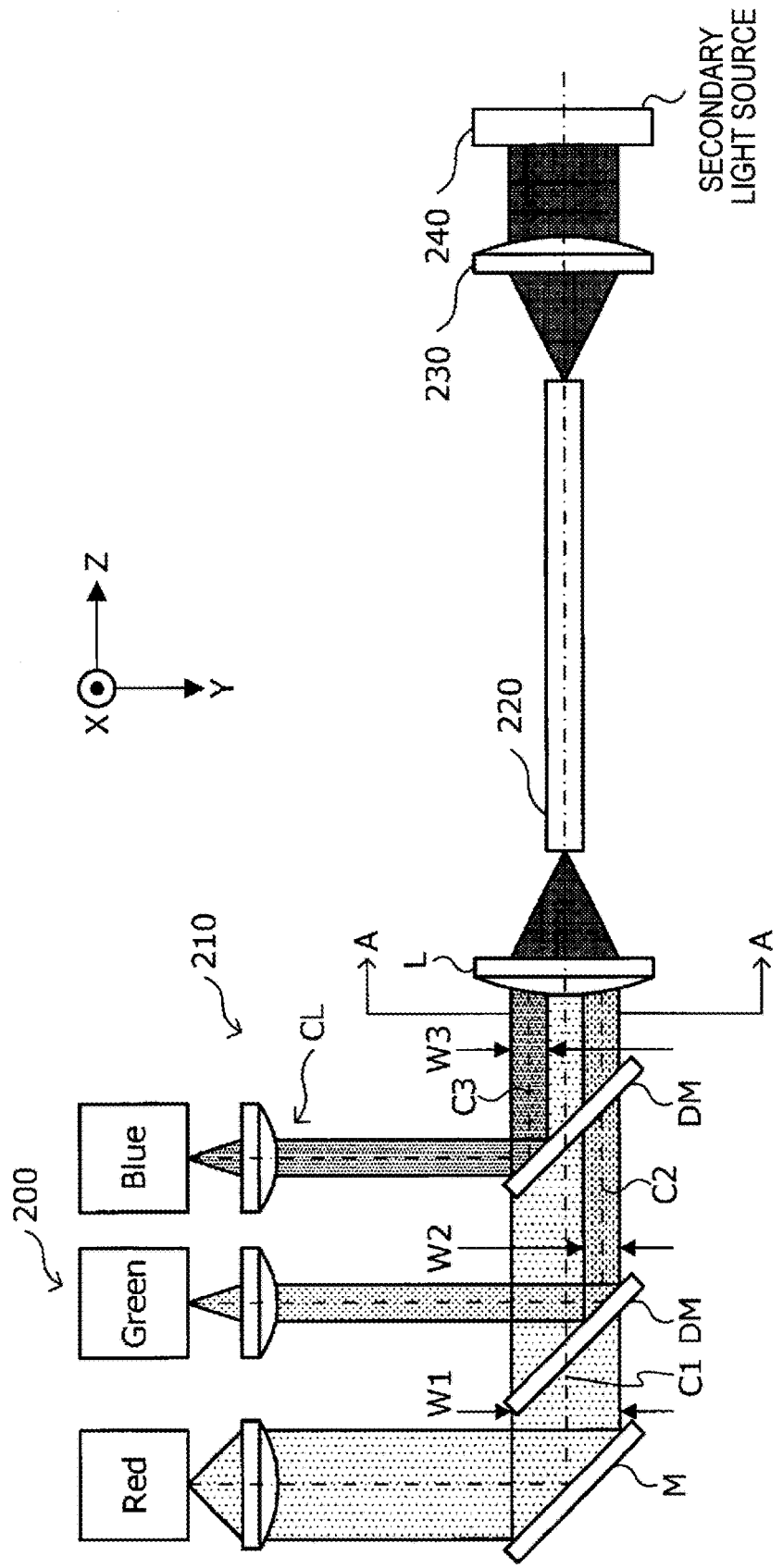

[Fig. 20]
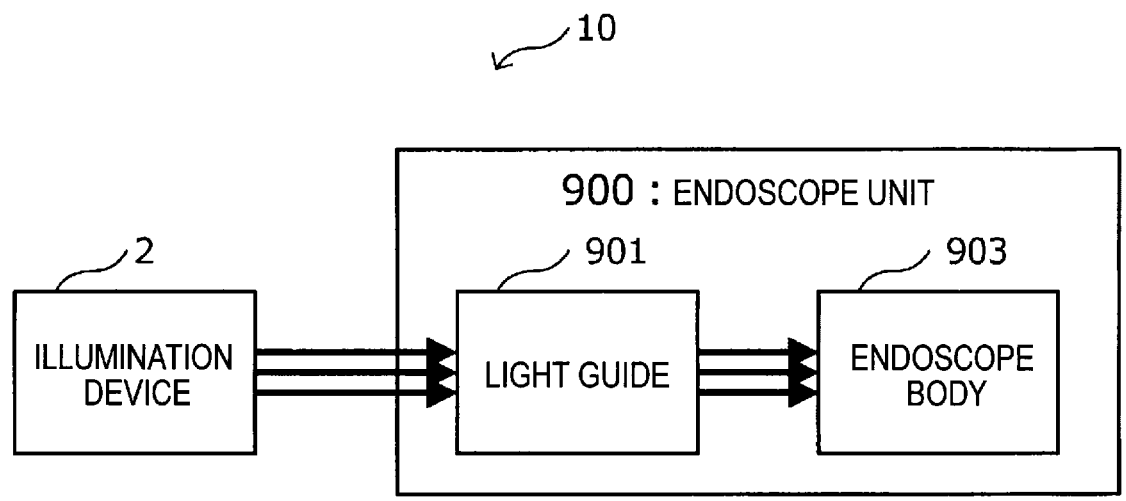

[Fig. 21]
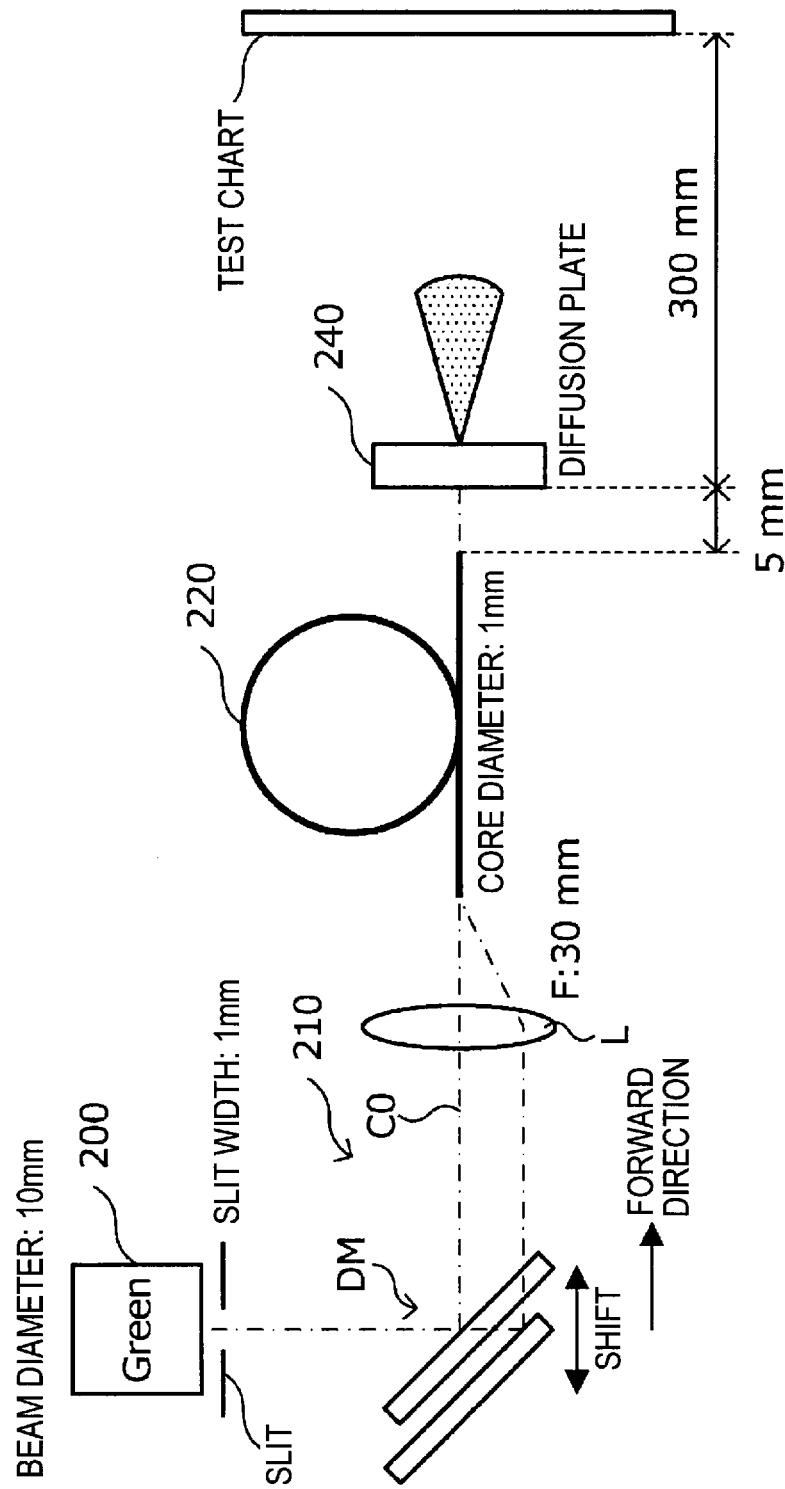

[Fig. 22]
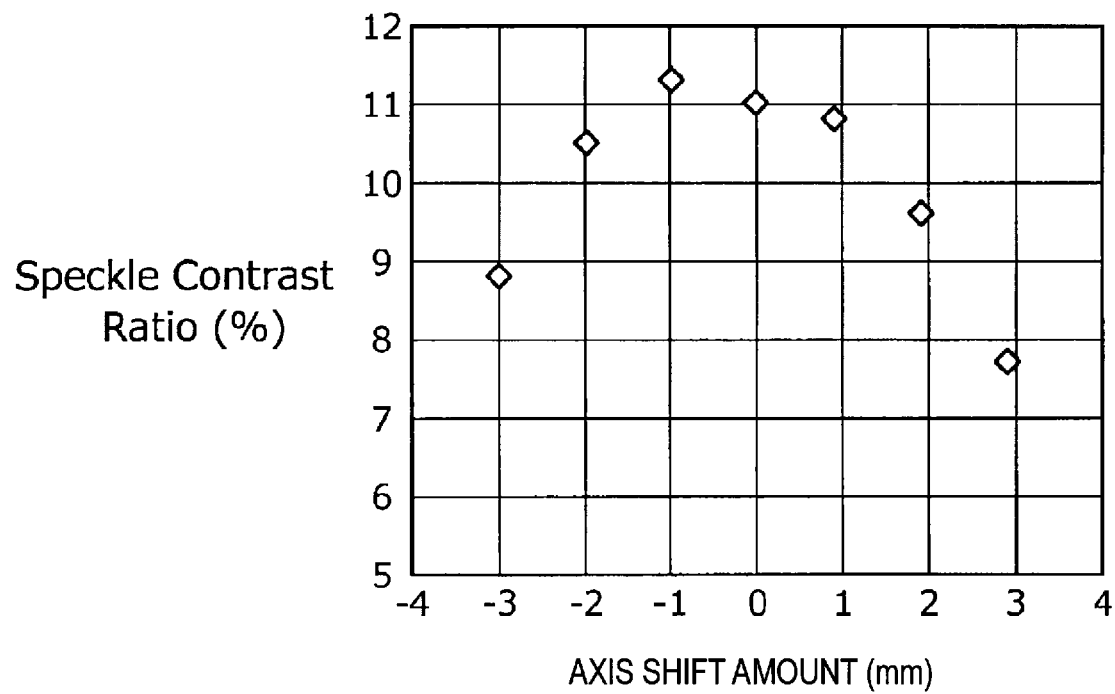

[Fig. 23]
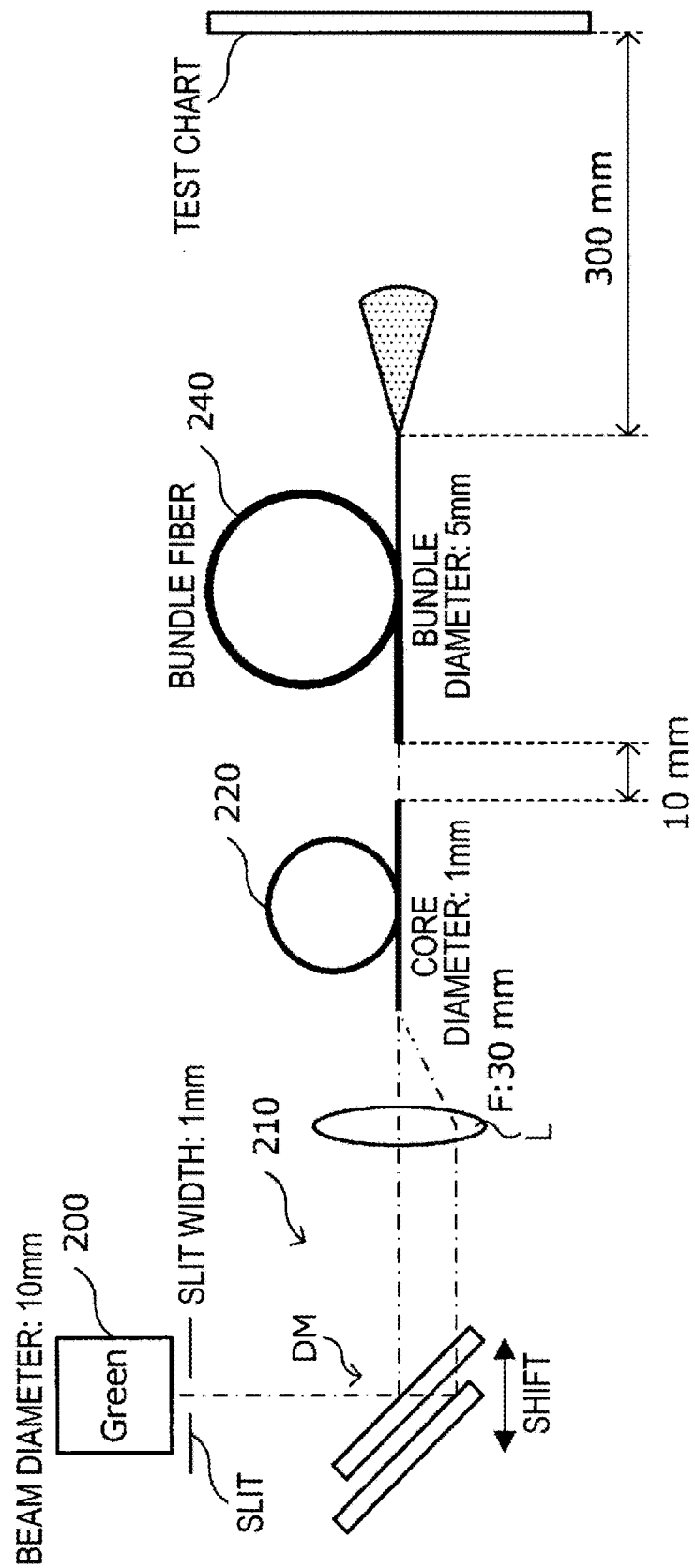

[Fig. 24]
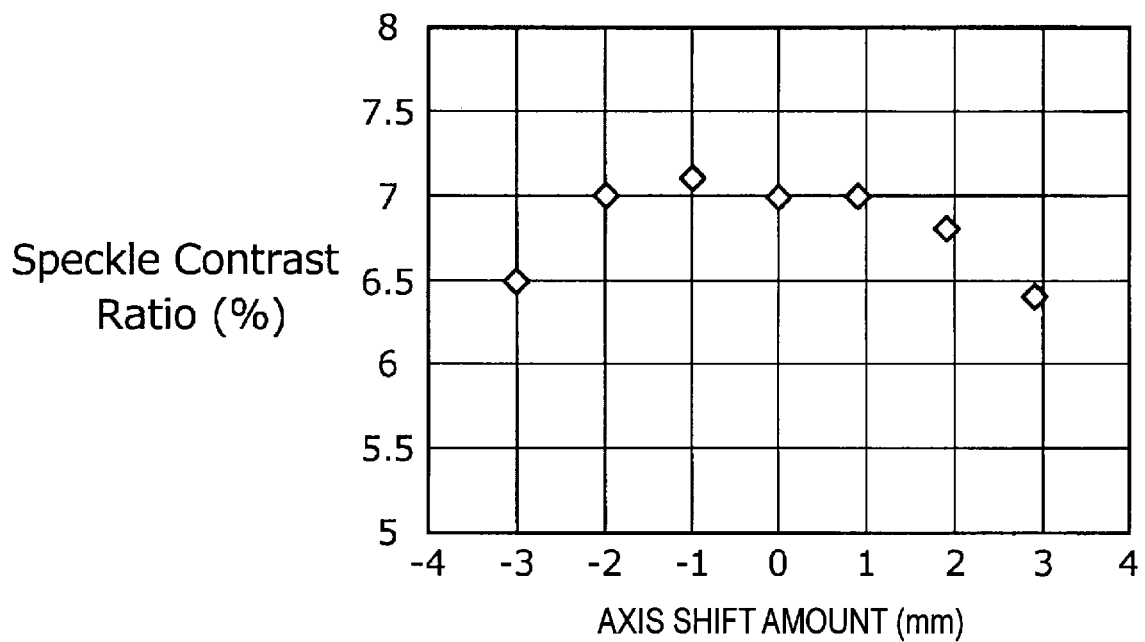

[Fig. 25]
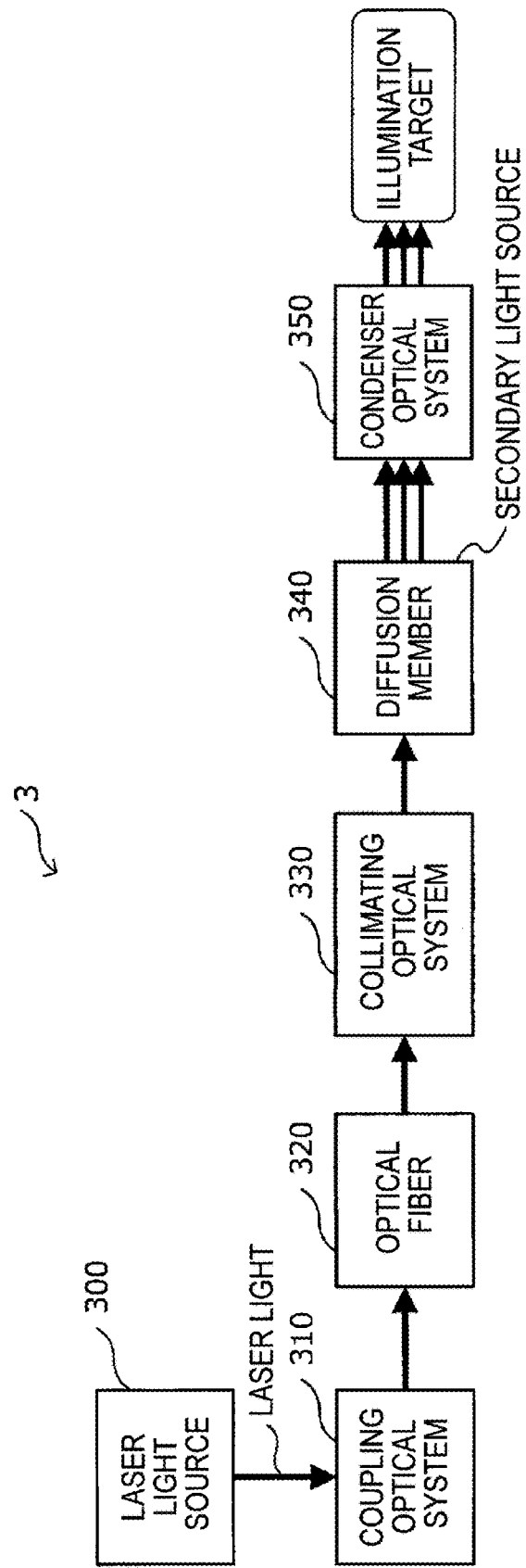

[Fig. 26]
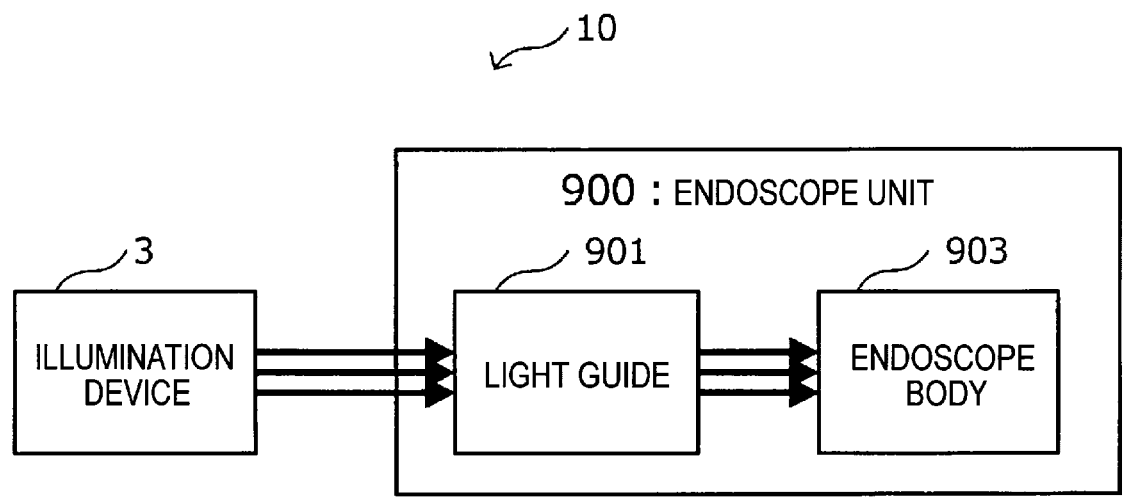

ILLUMINATION APPARATUS, METHOD AND MEDICAL IMAGING SYSTEM

CROSS REFERENCE TO RELATED APPLICATIONS

This Application is a national stage filing under 35 U.S.C. 371 of International Patent Application Serial No. PCT/JP2015/001705, filed Mar. 25, 2015, entitled "ILLUMINATION APPARATUS, METHOD AND MEDICAL IMAGING SYSTEM". Foreign priority benefits are claimed under 35 U.S.C. § 119(a)-(d) or 35 U.S.C. § 365(b) of Japanese Priority Patent Application JP 2014-111994 filed May 30, 2014, and Japanese Priority Patent Application JP 2014-111995 filed May 30, 2014, the entire contents of each of which are incorporated herein by reference.

TECHNICAL FIELD

The present disclosure relates to illumination devices, illumination methods, and endoscopes.

BACKGROUND ART

An optical system of an endoscope includes a light source, a condensing optical system, a light guide, which is a bundle fiber in which optical fibers are bundled, and an illuminating optical system. In general, a lamp light source such as a xenon lamp or a halogen lamp is often used as a light source for an endoscope. Light is emitted to an observation part from a distal end of a light guide by coupling the light from such a lamp light source with the light guide and connecting the light guide to a distal end of an endoscope insertion portion that will be inserted into a subject.

However, power consumption or a heating value of, particularly, a lamp light source such as a xenon lamp is considerable. Since a light distribution angle of a lamp light source is very broad, light efficiency is poor. Thus, as a light source for an endoscope, a laser has recently been used instead of a lamp light source.

Examples of the advantages obtained by using a laser as a light source are that (1) low power consumption of an illumination device can be expected since, for example, electrical-optical conversion efficiency of a light source is high and optical coupling efficiency to a light guide is high, (2) an endoscope insertion portion with a small diameter can be realized and optical coupling efficiency to a light guide with a small diameter is high because of the elevation of directivity of laser light, and (3) it is easy to observe a specific tissue with emphasis in combination with an optical absorption property of a tissue such as a blood vessel because a wavelength width is narrow.

However, when an object is illuminated with light emitted from an illumination device using a laser as a light source to observe a radiation field, bright and dark spots appear due to elevation of coherence of the laser light in some cases. This phenomenon occurs because random light interference occurs on a rough surface of the object and an interference pattern with a random intensity distribution appears. Such spots are called speckle noise and may disturb observation of the illumination field.

Accordingly, in order to obtain an observation image in which less speckle noise occurs, various technologies exemplified in PTL 1 to PTL 5 below have been proposed.

For example, PTL 1 below discloses an endoscope system that uses a bundle fiber in which a plurality of optical fibers are bundled with an optical path difference length equal to or greater than a coherence length as a noise reduction device.

For example, PTL 2 below discloses a light source device for an endoscope in which optical fibers are bundled using a plurality of modules outputting laser light with a modulated intensity by an optical fiber and optical coupling to a single optical fiber is further performed.

For example, PTL 3 below discloses an illumination device that includes a high-frequency superimposing unit that causes a semiconductor layer to perform multimode oscillation by superimposing a high-frequency signal on a driving current to be supplied to the semiconductor laser serving as a light source.

For example, PTL 4 below discloses an endoscope in which a vibration applying unit vibrating an optical fiber is disposed inside an endoscope insertion portion.

For example, PTL 5 below discloses an endoscope system that performs image processing on an obtained captured image and outputs the image as an observation image.

CITATION LIST

Patent Literature

PTL 1: JP 2008-043493A
PTL 2: JP 2009-240560A
PTL 3: JP 2010-042153A
PTL 4: JP 2010-172651A
PTL 5: JP 2012-005785A

SUMMARY

Technical Problem

However, a device is further used in addition to a bundle fiber device in which a wiring length is equal to or greater than the coherence length in PTL 1 above, a plurality of fiber light source devices and a plurality of intensity modulation devices in PTL 2 above, a high-frequency superimposing circuit in PTL 3 above, a mechanical vibration applying unit in PTL 4 above, and an image processing device in PTL 5, and a configuration for realizing the function of an illumination device. Therefore, the size of the entire device may increase and cost may be additionally necessary to reduce speckle noise.

It is desirable to provide an illumination device, an illumination method, and an endoscope capable of reducing speckle noise according to a simpler method.

Solution to Problem

Some embodiments relate to an illumination apparatus, comprising: an optical apparatus configured to optically process laser light to produce illumination light, the optical apparatus comprising: at least one collimator configured to collimate the laser light; and a diffuser configured to diffuse the laser light.

Some embodiments relate to medical imaging system, comprising: at least one laser light source configured to emit laser light; an illumination apparatus, including: an optical apparatus configured to optically process the laser light to produce illumination light, the optical apparatus comprising: at least one collimator configured to collimate the laser light; and a diffuser configured to diffuse the laser light; and a medical imaging device configured to receive the illumination light.

Some embodiments relate to an illumination method, comprising: optically processing laser light to produce illumination light, at least in part by: A) collimating the laser light; and B) diffusing the laser light.

Advantageous Effects of Invention

According to an embodiment of the present disclosure described above, it is possible to reduce speckle noise according to a simpler method.

Note that the effects described above are not necessarily limited, and along with or instead of the effects, any effect that is desired to be introduced in the present specification or other effects that can be expected from the present specification may be exhibited.

BRIEF DESCRIPTION OF DRAWINGS

FIG. 1A is an explanatory diagram schematically illustrating the configuration of an illumination device according to a first embodiment of the present disclosure.

FIG. 1B is an explanatory diagram schematically illustrating an inlet end of a light guide.

FIG. 2 is an explanatory diagram schematically illustrating the configuration of the illumination device according to the embodiment.

FIG. 3 is an explanatory diagram schematically illustrating the configuration of the illumination device according to the embodiment.

FIG. 4 is an explanatory diagram for describing a positional relation between a pupil position of a collector lens and laser light.

FIG. 5 is an explanatory diagram for describing a positional relation between a pupil position of a collector lens and laser light.

FIG. 6 is an explanatory diagram for describing a positional relation between a pupil position of a collector lens and laser light.

FIG. 7 is an explanatory diagram for describing a positional relation between a pupil position of a collector lens and laser light.

FIG. 8 is a graph illustrating a relation between speckling and a shift amount on an optical axis of a dichroic mirror.

FIG. 9A is an explanatory diagram for describing a positional relation between a pupil position of a collector lens and laser light.

FIG. 9B is an explanatory diagram for describing a positional relation between a pupil position of a collector lens and laser light.

FIG. 10 is an explanatory diagram schematically illustrating the configuration of an endoscope including the illumination device according to the embodiment.

FIG. 11 is an explanatory diagram illustrating lens data of a condenser according to the embodiment.

FIG. 12A is an explanatory diagram illustrating a lens configuration example of the condenser according to the embodiment.

FIG. 12B is an explanatory diagram illustrating a lens configuration example of the condenser according to the embodiment.

FIG. 12C is an explanatory diagram illustrating a lens configuration example of the condenser according to the embodiment.

FIG. 13A is an explanatory diagram schematically illustrating the configuration of an illumination device according to a second embodiment of the present disclosure.

FIG. 13B is an explanatory diagram schematically illustrating the configuration of the illumination device according to the embodiment.

FIG. 14A is an explanatory diagram schematically illustrating the configuration of the illumination device according to the embodiment.

FIG. 14B is an explanatory diagram schematically illustrating the configuration of the illumination device according to the embodiment.

FIG. 14C is an explanatory diagram schematically illustrating the configuration of the illumination device according to the embodiment.

FIG. 15 is an explanatory diagram schematically illustrating the configuration of the illumination device according to the embodiment.

FIG. 16 is an explanatory diagram schematically illustrating the configuration of the illumination device according to the embodiment.

FIG. 17 is an explanatory diagram schematically illustrating the configuration of the illumination device according to the embodiment.

FIG. 18A is an explanatory diagram for describing a positional relation between a pupil position of a collector lens and laser light.

FIG. 18B is an explanatory diagram for describing a positional relation between a pupil position of a collector lens and laser light.

FIG. 19 is an explanatory diagram schematically illustrating the configuration of the illumination device according to the embodiment.

FIG. 20 is an explanatory diagram schematically illustrating the configuration of an endoscope including the illumination device according to the embodiment.

FIG. 21 is an explanatory diagram schematically illustrating a device configuration for verifying a relation between speckling and a shift amount on an optical axis of a dichroic mirror.

FIG. 22 is a graph illustrating a relation between the speckling and the shift amount on the optical axis of the dichroic mirror.

FIG. 23 is an explanatory diagram schematically illustrating a device configuration for verifying a relation between speckling and a shift amount on an optical axis of a dichroic mirror.

FIG. 24 is a graph illustrating a relation between the speckling and the shift amount on the optical axis of the dichroic mirror.

FIG. 25 is an explanatory diagram schematically illustrating the configuration of an illumination device according to a third embodiment of the present disclosure.

FIG. 26 is an explanatory diagram schematically illustrating the configuration of an endoscope including the illumination device according to the embodiment.

DESCRIPTION OF EMBODIMENTS

Hereinafter, preferred embodiments of the present disclosure will be described in detail with reference to the appended drawings. Note that, in this specification and the appended drawings, structural elements that have substantially the same function and structure are denoted with the same reference numerals, and repeated explanation of these structural elements is omitted.

The description will be made in the following order.
1. Speckle noise
2. First embodiment (example of reduction of speckle noise of entire illumination device)

2.1. Configuration of illumination device
2.2. Configuration of endoscope
2.3 Specific example of condenser
3. Second embodiment (example in which portions related to spatial coherence in speckle noise observed in light sources are almost equalized by reducing speckle noise of light sources)
3.1. Configuration of illumination device
3.2. Configuration of endoscope
3.3. Verification example
4. Third embodiment (combination example of first and second embodiments)

Speckle Noise

Before an illumination device, an illumination method, and an endoscope according to an embodiment of the present disclosure are described, speckle noise (hereinafter also simply referred to as "speckling") to be focused on in an embodiment of the present disclosure will be described in brief.

The speckle noise is known to depend on (a) a wavelength width of a light source illuminating an observation part, (b) a luminance distribution of the light source illuminating the observation part, and (c) surface roughness of the observation part. Of the three factors, (a) is related to temporal coherence of the light source and (b) is related to spatial coherence of the light source. Accordingly, the speckling treated as a problem herein is related to the spatial coherence of the light source.

Coherence of an object surface illuminated by a light source with a luminance distribution S(xi) is known to obey the theorem of Van Cittert Zernike expressed as Expression 1 below.

[Math. 1]

$$\mu(x, x + \Delta x) = \frac{1}{\int d\zeta S(\zeta)} \int d\zeta S(\zeta) \exp\left[-i\frac{2\pi}{\lambda}\zeta \Delta x\right] \quad \text{(Expression 1)}$$

Here, in Expression 1 above,
x is a position on an object surface,
mu is a complex coherence degree (a parameter indicating spatial coherence between positions x and (x+change in x),
S(xi) is a luminance distribution of a light source,
i is an imaginary unit, and
lambda is a wavelength.

As is apparent from the form of Expression 1 above, the spatial coherence of an object surface is given by Fourier transform of the luminance distribution S(xi) of a light source. That is, a space frequency spectrum of the luminance distribution of the light source is the coherence degree. Accordingly, when the light source is a point light source, the luminance distribution S(xi) can be considered as a delta function. All of the points on an object surface interfere with each other, and the coherence increases. Such a light source (point light source) is referred to as a coherence light source. On the other hand, when the light source is a uniform light source with an infinite size, the luminance distribution S(xi) is equal to 1. Thus, the Fourier transform becomes a delta function. Interference occurs only at the same position on an object surface and the coherence decreases. The light source with an infinite size is referred to as an incoherent light source. A light source actually used in an illumination device is a partially coherent light source positioned between a spatially coherent light source and an incoherent light source. Therefore, the coherence decreases as the size of a light source is apparently larger and the luminance distribution of the light source is more uniform.

In recent years, for a laser used as a light source, a wavelength width is narrower and the size of a light emission portion is smaller than those of a lamp light source because of its light emission principle. Therefore, spatial and temporal coherence of light is high. As a result, when a laser is used as a light source, the speckle noise tends to be considerably observed.

Here, in order to obtain white light using laser light, using laser devices emitting R (red light), G (green light), and B (blue light) which are the three primary colors of light can be considered, or adding light emitted by a B laser device and a fluorescent substance for blue light excitation can be considered. However, since a near-field pattern (NFP) or a far-field pattern (FFP) differs for each color laser device, color unevenness occurs and a difference in the spatial coherence originating from a beam shape occurs. As a result, the size of the speckle noise observed in each color may differ.

For one invariant maintained in the entire optical system, there is a Lagrangian invariant expressed by Expression 2 below.

[Math. 2]

$$L_1 = \varphi_1 \times NA_1 \quad \text{(Expression 2)}$$

$L_1$: Lagrangian invariant
$\varphi_1$ size of light source
$NA_1$: numerical aperture of light source(=n×sin $\Theta_1$)
n: refractive index
$\Theta_1$: divergence angle of light source Here, in an optical system using a laser, since the foregoing Lagrangian invariant is small, it is difficult to cause a large divergence angle and the size of a large light source necessary in coupling of a light guide to be compatible.

Accordingly, when an illumination light source is realized for an endoscope using a laser, it is necessary to sufficiently consider the foregoing points.

When a coherent light source such as a laser is used and a beam diameter is set to be small at an inlet end of the light guide by focusing on only an improvement in optical coupling efficiency to the light guide, the coherence increases as is apparent from the foregoing description and the speckle noise occurs more easily. As countermeasures for reducing the speckling, as disclosed in PTL 1 to PTL 5 above, reduction in the speckle noise is attempted by further adding a mechanism to an illumination device in the related art.

The present inventors, through intensive investigation, have come up with the idea of reducing the speckle noise more simply by focusing on a luminance distribution and a beam diameter of laser light, and thus an illumination device and an illumination method according to embodiments of the present disclosure to be described below have been finalized. An illumination device and an illumination method according to embodiments of the present disclosure and an endoscope using the illumination device will be described in detail below.

First Embodiment

Hereinafter, the illumination device and the illumination method capable of diminishing speckle noise by reducing coherence in the entire illumination device and the endoscope including the illumination device will be described in detail.

Configuration of Illumination Device

First, the configuration of the illumination device according to a first embodiment of the present disclosure will be described with reference to FIGS. 1A to 9B. FIG. 1A is an explanatory diagram schematically illustrating the configuration of the illumination device according to the embodiment. FIG. 1B is an explanatory diagram schematically illustrating an inlet end of a light guide. FIGS. 2 and 3 are explanatory diagrams schematically illustrating the configuration of the illumination device according to the embodiment. FIGS. 4 to 7 and 9A to 9B are explanatory diagrams for describing a positional relation between a pupil position of a collector lens and laser light. FIG. 8 is a graph illustrating a relation between speckle and a shift amount on an optical axis of a dichroic mirror.

As schematically illustrated in FIG. 1A, an illumination device 1 according to the embodiment includes a laser light source 100, a coupling optical system 110, an optical fiber 120, a collimator 130, a diffuser 140, and a condenser 150.

At least one laser light source 100 is installed in the illumination device 1 and emits laser light with a predetermined wavelength. In the illumination device 1 according to the embodiment, various semiconductor lasers or solid-state lasers can be used as the laser light sources 100, and a combination of the lasers and a wavelength conversion mechanism can also be used. The wavelength of the laser light emitted from the laser light source 100 may be appropriately selected according to which object or phenomenon is observed in an illumination target. Examples of the wavelength include the visible light band of wavelengths from about 400 nm to about 700 nm or a nearinfrared band used for ICG (Indocyanine green) fluorescence imaging. When the laser light is used as excited light for fluorescence excitation, observed fluorescence may include autofluorescence of a part irradiated with the excited light or chemical agent fluorescence originating from various fluorescent reagents introduced into an irradiated part.

The coupling optical system 110 is an optical system that optically couples the laser light emitted from the laser light source 100 with the optical fiber 120 installed at the rear stage. The configuration of the coupling optical system 110 is not particularly limited. The coupling optical system 110 may be appropriately combined with various optical elements of the related art to optically couple the laser light with the optical fiber 120 and includes at least one condensing lens (collector lens) that optically couples the laser light with the optical fiber 120.

When the plurality of laser light sources 100 are combined to realize white illumination light, at least one dichroic mirror or dichroic prism is further installed in addition to the collector lens in the coupling optical system 110. A plurality of beams of laser light emitted from the plurality of laser light sources 100 are multiplexed by the dichroic mirror or the dichroic prism to generate white light. The multiplexed light is condensed by the collector lens to be coupled to the optical fiber 120.

When the plurality of laser light sources 100 are used in combination, the numerical apertures on which the laser light is incident on the optical fiber 120 are preferably aligned. However, because the FFP of each laser differs, it is difficult to align the numerical apertures of incidence in practice. Accordingly, in this case, in the coupling optical system 110, a numerical aperture adjustment unit that aligns the numerical apertures of incidence between the laser light emitted from the laser light sources 100 is installed. The numerical aperture adjustment unit will be described again later in detail.

The optical fiber 120 guides the laser light guided by the coupling optical system 110 to the collimator 130 installed at the rear stage. The light emitted from the optical fiber 120 becomes a rotationally symmetric beam, which contributes to uniformity of a luminance distribution. The optical fiber 120 is not particularly limited, but a multimode optical fiber (for example, a step-index type multimode fiber) of the related art can be used. The core diameter of the optical fiber 120 is not particularly limited either. For example, an optical fiber with a core diameter of about 1 mm can be used.

In the optical fiber 120 according to the embodiment, light is guided to an inlet end of the optical fiber 120 so that the numerical apertures between the plurality of light sources accord as much as possible at the inlet end of the optical fiber. At this time, for example, by optimizing a focal distance of a lens collimating the laser light emitted from the laser light sources, the laser light emitted from an emission end of the optical fiber 120 preferably becomes a solid beam for which the amount of light in the vicinity of the central optical axis of the optical fiber is equal to that of the peripheral portion of the optical fiber, rather than a beam with a doughnut form in which the amount of light in the vicinity of the central optical axis of the optical fiber is less than the amount of light of the peripheral portion.

The collimator 130 is installed downstream from the exit end of the optical fiber 120 and converts the laser light emitted from the optical fiber 120 into a parallel light flux. By converting the laser light into the parallel light flux by the collimator 130, a diffusion state of the laser light can be easily controlled by a diffusion angle of the diffuser 140 in the diffuser 140 installed at the rear stage. The configuration of the collimator 130 is not particularly limited, but optical elements of the related art may be appropriately combined so that an optical system of the related art is configured to convert the laser light into the parallel light flux.

The diffuser 140 is installed near a rear focal position of the collimator 130 and diffuses the parallel light flux emitted from the collimator 130 to generate a secondary light source. That is, the emission end of the light in the diffuser 140 functions as the secondary light source.

The size of the secondary light source generated by the diffuser 140 can be controlled by the focal distance of the collimator 130. NA of the exited light can be controlled by the diffusion angle of a diffusion plate. The Lagrangian invariant indicated by Expression 2 above can be enlarged by the effects of both of the constituents, and thus a desired light source size and a desired illumination range can be compatible.

When the size of the secondary light source is desired to be adjusted, the size of the secondary light source may be optimized by the exit NA from the optical fiber and the focal distance of the collimator. An actual range in which the vicinity of the rear focal position falls is not particularly limited. For example, the range of the focal distance plus or minus about 10% upstream and downstream from the rear focal position including the rear focal position is preferable.

A divergence angle of the light emitted from the diffuser 140 is controlled by the diffusion angle of the diffuser 140. Further, an exit angle when the parallel light flux at an angle of view omega (degrees) is transmitted through the diffuser (for example, a diffusion plate) approximates Expression 101 below.

[Math. 3]

$$\Theta = \sqrt{\Theta_w^2 + \Theta_d^2} \qquad \text{(Expression 101)}$$

Here, in Expression 101 above,
theta is an exit angle of the diffuser, theta$_w$ is an angle of view of incident light, and
theta$_d$ is a diffusion angle of the diffuser.

The diffusion angle theta$_d$ of the diffuser is assumed to be equal to 23 degrees and the core diameter w of the optical fiber 120 (multimode fiber) is assumed to be equal to 1 mm. The angle of view theta$_w$ of incident light is given as theta$_w$=a tan {(w/2)/f$_{col}$} when f$_{col}$ is the focal distance of the collimator 130. Therefore, for example, when f$_{col}$=7.9 mm is set with reference to the focal distance of the collimator, theta$_w$ is equal to 3.6 degrees. When theta$_d$ and theta$_w$ are substituted into Expression 101 above, the exit angle theta of the diffuser is equal to 23.27 degrees. This result indicates that when the core diameter of the multimode fiber is about the foregoing diameter at the exit angle theta of the diffuser, the influence of the angle of view theta$_w$ is rarely present and on-axis light and off-axis light are both controlled at the diffusion angle set in the diffuser 140.

In the embodiment, the diffusion angle of the diffuser 140 is not particularly limited, but may be appropriately decided according to a size of the illumination device 1 to be realized, characteristic values of the diffuser applicable to the illumination device 1, or the like. The diffusion angle theta$_d$ can be set to, for example, about 23 degrees.

The kind of specific diffuser 140 is not particularly limited, but a diffusion element of the related art can be used. Examples of the diffuser include a frost type obscure glass, an opal type diffusion plate using diffusion characteristics, for example, by diffusing an optical diffusion material into glass, and a holographic diffusion plate. The holographic diffusion plate is particularly preferred since a holographic pattern is applied to a predetermined substrate and any angle is set as a diffusion angle of exited light.

The light emitted from the diffuser 140 is guided to the condenser 150. The condenser 150 forms an image of the secondary light source formed by the diffuser 140 to an illumination target at a predetermined paraxial lateral magnification. An example of the illumination target includes an inlet end of a light guide located downstream from the condenser 150 and installed in an endoscope unit. As schematically illustrated in FIG. 1B, a plurality of optical fibers including a fiber core portion and a fiber clad portion are structured to be bundled at the inlet end of the light guide. Here, the condenser 150 according to the embodiment is different from that of the related art and forms an image of the secondary light source so that the area of the illumination target (for example, the inlet end of the light guide installed in the endoscope unit) is filled as much as possible. Thus, the illumination device 1 can reduce the speckle noise as a whole.

An image formation magnification (paraxial lateral magnification) beta of the condenser 150 is expressed by Expression 102 below by a focal distance f of the condenser and a distance X between the focal position F and an object surface.

[Math. 4]

$$\beta = f/X \quad \text{(Expression 102)}$$

Here, when the condenser 150 is aplanatic, the image formation magnification beta of the condenser 150 and a numerical aperture of incidence and an exit numerical aperture of the condenser 150 satisfy a relation expression expressed as Expression 103 below.

[Math. 5]

$$\beta = Y'/Y = NA_{cond}/NA_{cond}' \quad \text{(Expression 103)}$$

Y: size of secondary light source
Y': size of image of secondary light source
NA$_{cond}$: numerical aperture of incidence of condenser optical system
NA$_{cond}$': exit numerical aperture of condenser optical system On the other hand, when NA$_L$ is an allowable numerical aperture of the light guide which is a bundle fiber in which the optical fibers are bundled, n$_1$ is a refractive index of the core portion of the optical fiber, and n$_2$ is a refractive index of the clad portion, Expression 104 below is given. The allowable numerical aperture NA$_L$ of a general light guide is in the range of greater than or equal to 0.56 and less than or equal to 0.88.

[Math. 6]

$$NA_L = \sqrt{n_1^2 - n_2^2} \quad \text{(Expression 104)}$$

A relation of Expression 105 below is preferably satisfied in order for the condenser 150 to condense the light from the light source and in order to cause the light to be efficiently incident on the light guide installed at the rear stage of the condenser 150.

[Math. 7]

$$NA_{cond}' \leq NA_L \quad \text{(Expression 105)}$$

Further, in the illumination device 1 according to the embodiment, the size of an image of the secondary light source is preferably controlled so that a relation expressed by Expression 106 below is established when phi$_{LG}$ is the diameter of the inlet end of the light guide on which the secondary light source transmitted through the condenser 150 is incident and Y' is the size of the image of the secondary light source. That is, the image of the secondary light source preferably fills the inlet end of the light guide. By satisfying a relation expression expressed as Expression 106 below, it is possible to plan a reduction in the speckle noise while satisfying the relation expression expressed as Expression 105 above. The size of the image of the secondary light source is defined by emission NA of the multimode fiber and a focal distance of a collimator.

[Math. 8]

$$0.8 \leq Y'/\varphi_{LG} \leq 1.2 \quad \text{(Expression 106)}$$

When Y'/phi$_{LG}$ is less than 0.8, the image of the secondary light source becomes smaller than the diameter of the inlet end of the light guide. The inlet end and the emission end of the light guide are generally conjugated. Consequently, when an illuminated surface is illuminated with the light emitted from the light guide, the size of the light source apparent from the illuminated surface becomes small and the speckling may deteriorate. When the secondary light source is controlled so as to be sufficiently smaller than the core diameter in terms of the optical coupling efficiency, there is a high probability of the speckling deteriorating when a spot size is small. When an endoscope is configured such that the light guide is branched halfway and illumination is performed at a plurality of exit ends, a luminance distribution may differ between the branched exit ends and there is a problem that the speckling may deteriorate.

Conversely, when Y'/phi$_{LG}$ is greater than 1.2, the secondary light source or the image of the secondary light source becomes larger than the diameter of the inlet end of the light guide. In this case, vignetting of laser light occurs on an inlet end surface of the light guide and the optical coupling efficiency may be lowered.

A relation of $Y'=\phi_{LG}$ is more preferably established between the size $Y'$ of the image of the secondary light source and the diameter $\phi_{LG}$ of the inlet end of the light guide at which the image of the secondary light source formed by the condenser is formed.

The paraxial lateral magnification beta of the condenser 150 may be decided appropriately so that the size $Y'$ of the image of the secondary light source satisfies the range of Expression 106 above and is more preferably greater than or equal to 0.4 and less than or equal to 2.3.

When the paraxial lateral magnification beta is less than 0.4, an effective diameter of the diffuser 140 becomes too large and there is a probability of the device increasing in size. Thus, it is not desirable for paraxial lateral magnification beta to be less than 0.4. Conversely, when the paraxial lateral magnification beta is greater than 2.3, a large diffusion angle is necessary for the diffuser 140 and there is a probability of transmittance deteriorating. It is necessary for the diffuser 140 to have a special structure separately, and thus there is a probability of cost increasing. When the paraxial lateral magnification beta of the condenser 150 is in the foregoing range, it is possible to achieve miniaturization of the device while suppressing manufacturing cost of the illumination device. As a method of adjusting the size $Y'$ of the image of the secondary light source so that Expression 106 is satisfied, a mechanism capable of adjusting an interval between the condenser lens and the inlet end surface of the light guide may be installed.

The configuration of the illumination device 1 according to the embodiment has been described in detail above with reference to FIGS. 1A and 1B.

Specific Example of Illumination Device

Next, the configuration of the illumination device according to the embodiment will be described specifically with reference to FIGS. 2 to 9B.

FIG. 2 schematically illustrates the configuration of the illumination device 1 when laser light sources emitting red light, green light, and blue light are used as the laser light sources 100 and a holographic diffusion plate 141 is used as the diffuser 140. FIG. 3 schematically illustrates the configuration of the illumination device 1 when the laser light sources emitting red light, green light, and blue light are used and a microlens array 143 is used as the diffuser 140.

As illustrated in FIGS. 2 and 3, the beams of laser light emitted from the RGB laser light sources are multiplexed by a mirror M or a dichroic mirror DM to be guided to a collector lens L. As illustrated in FIGS. 2 and 3, when a plurality of lasers are used as the light sources, a difference in a beam diameter of each color occurs at the pupil position of the collector lens L, for example, as schematically illustrated in FIG. 4.

As described above, when the RGB colors are coupled to the optical fiber 120 by the collector lens L, the numerical apertures of incidence to respective color optical fibers are preferably aligned. This is for the following reason. In general, since power placement of a lens is decided according to laser light for which the numerical aperture of incidence is largest, the beam diameter of laser light for which the numerical aperture of incidence is small may become small at the position of a diffusion plate. That is, a luminance distribution at the inlet end of the light guide may become nonuniform. In order to align the numerical apertures of incidence of the respective colors, for example, there is a method of matching the apparent beam diameters of the respective colors at the pupil position of the collector lens L. In this method, for example, as schematically illustrated in FIG. 5, an end portion of the laser light with the smallest beam diameter may be located at a position (that is, an end portion of the laser light with the largest beam diameter) at which the numerical aperture of incidence is the largest. By doing so, the laser light with the largest beam diameter and the laser light with the smallest beam diameter come into contact with each other at a certain point. In FIG. 5, the end portions of the two beams of laser light come into contact with each other in the positive direction of a xi axis, but the position is not limited to the case illustrated in FIG. 5. The end portions may come into contact with each other in the negative direction of the xi axis.

When a plurality of lasers with the same wavelength or close wavelengths are multiplexed because of guarantee of an output, the reduction in the temporal coherence, or the like, the beam with the smallest beam diameter may be disposed at least at the center of the pupil and the position at which the numerical aperture of incidence is the largest, as schematically illustrated in FIG. 6.

By equalizing the numerical apertures, as schematically illustrated in FIGS. 5 and 6, the light quantity distribution of the secondary light source formed at the position of the diffuser 140 becomes uniform, and thus it is possible to reduce a difference in the amount of speckling occurring due to the colors. In other words, the largest beam diameters of the secondary light sources of the colors formed by the diffuser 140 are substantially equivalent, and thus it is possible to reduce the difference in the amount of the speckling occurring due to the colors.

In order to realize the situation illustrated in FIG. 5, a position on which the laser light is incident on the collector lens L may be adjusted using the dichroic mirror DM installed as one constituent of the coupling optical system 110 as a numerical aperture adjustment unit.

Specifically, when a laser light source A emitting laser light with a larger beam diameter and a laser light source B emitting laser light with a smaller beam diameter are present, as illustrated in FIG. 7, the beam position may be offset, as illustrated in FIG. 5, by shifting the dichroic mirror DM in an optical axis direction of the disposition position of the dichroic mirror DM with respect to the central optical axis of the coupling optical system 110. Thus, as illustrated in FIG. 5, the mutual beam positions can be matched.

In practice, a result obtained by shifting the dichroic mirror with the above configuration is illustrated in FIG. 8. The horizontal axis of FIG. 8 represents a shift amount of the dichroic mirror DM with respect to the central optical axis of the coupling optical system 110 and the vertical axis of FIG. 8 represents a speckle contrast ratio (SCR) corresponding to the amount of speckling. As is apparent from FIG. 8, it can be understood that the luminance distribution at the inlet end of the light guide is close to uniformity by the shift and the speckle contrast is thus reduced.

In order to realize the situation illustrated in FIG. 6, a position on which the laser light is incident on the dichroic mirror DM may be adjusted further using the mirror M or a lambda/2-wavelength plate, or a polarized beam splitter PBS as a numerical aperture adjustment unit, for example, as illustrated in FIGS. 9A and 9B.

The laser light source emitting the laser light with the large beam diameter can also be realized by setting the paraxial lateral magnification of the condenser 150 without providing the numerical aperture adjustment unit so that Expression 106 above is satisfied. The laser light source emitting the laser light with the small beam diameter can also be realized by adjusting the numerical aperture using the numerical aperture adjustment unit so that Expression 106 above is satisfied.

The configuration of the illumination device according to the embodiment has been described specifically above with reference to FIGS. 2 to 9B.

Configuration of Endoscope

Next, the configuration of the endoscope 10 in which the illumination device 1 according to the embodiment is used as an illumination light source will be described in brief with reference to FIG. 10. FIG. 10 is an explanatory diagram schematically illustrating the configuration of an endoscope including the illumination device according to the embodiment.

The image of the light source by the condenser is formed in a light guide 901 included in any endoscope unit 900 by using the above-described illumination device 1 as a light source so that illumination light with reduced speckle noise can be obtained. The illumination light guided to the light guide 901 is guided to an endoscope body 903 by the light guide 901 to be guided to a distal end portion of the endoscope.

Here, the endoscope unit 900 on which the illumination device 1 is mounted is not particularly limited, but any endoscope unit can be used as long as the endoscope unit 900 includes the general light guide 901. In contrast, when the endoscope unit 900 including the specific light guide 901 is desired to be used, the size Y' of the image of the secondary light source of the illumination device 1 according to the embodiment or the paraxial lateral magnification beta of the condenser 150 may be set according to the allowable numerical aperture $NA_L$ of incidence of the light guide 901.

The endoscope 10 including the illumination device 1 according to the embodiment has been described in brief above with reference to FIG. 10.

Specific Example of Condenser

Next, a specific example of the condenser 150 in the illumination device 1 according to the embodiment will be described with reference to FIGS. 11 to 12C. FIG. 11 is an explanatory diagram illustrating lens data of the condenser according to the embodiment. FIGS. 12A to 12C are explanatory diagrams illustrating lens configuration examples of the condenser according to the embodiment.

The lens data of the specific example of the condenser 150 according to the embodiment is illustrated in FIG. 11 and the lens configuration diagrams are illustrated in FIGS. 12A to 12C. In tables illustrated in FIG. 11, f is a focal distance, S1 to H are a distance between a first surface of a condenser lens system and a front side main point position, beta is a paraxial lateral magnification, OBJ is a distance between the first surface and an object surface, and X is a distance between the focal position F to the object surface. In the table on the upper side of FIG. 11, the lens data of columns A to C corresponds to the lens configuration diagrams illustrated in FIGS. 12A to 12C, respectively.

In the condenser 150 illustrated in FIGS. 11 to 12C, a case in which the light guide 901 with the diameter $phi_{LG}$=2.0 of the surface of incidence on the light guide and the allowable numerical aperture $LA_L$=0.57 is used is assumed. Other set values of the illumination device 1 are as follows.

multimode fiber exit numerical aperture $NA_M$=0.22
collimator focal distance $f_{col}$=7.6
size Y of secondary light source=3.34
diffusion plate angle=23 degrees As illustrated in FIGS. 12A to 12C, in each specific example of the condenser 150 according to the embodiment, an surface of incidence (a surface located on the right side of the drawing in FIGS. 12A to 12C) on the secondary light source side and an exit surface (a surface located on the left side of the drawing in FIGS. 12A to 12C) on an image side of the second light source are formed by plane lens systems. As is apparent from the table on the lower side of FIG. 11 and FIGS. 12A to 12C, the condenser 150 is formed by a lens system that includes a positive plano-convex lens with a plane oriented toward the diffuser, one or more positive lenses, and a positive plano-convex lens with a plane oriented toward the rear end of the condenser 150 in order from the side of the diffuser 140. The surface (corresponding to a surface number S=7 in the lens data illustrated on the lower side of FIG. 11) of the plano-convex lens, which is located closest to the image side of the secondary light source, on the side of the diffuser 140 is set to be an aspheric surface.

An aspheric surface that is rotationally symmetric about an optical axis is expressed by Expression 107 blow. Here, in Expression 107 below, C is curvature (1/r), h is a height from the optical axis, and K is a conical constant. Aspheric surface data of the surface number S=7 is illustrated on the lower side of FIG. 11.

[Math. 9]

$$x = \frac{Ch^2}{1 + \sqrt{1 - (1+K)C^2h^2}} + (A4)h^4 + (A6)h^6 + (A8)h^8 + \ldots \quad \text{(Expression 107)}$$

In the condenser 150 according to the embodiment, low cost can be achieved by using the lenses illustrated in FIGS. 11 to 12C.

In particular, in the case of the lens configuration illustrated in FIG. 12B, since beta is equal to 0.6 and Y is equal to 3.34, Y' is equal to 2 and Expression 106 is satisfied. Further, NA is equal to 0.57, Expression 105 is established, and thus the illumination light can be coupled to the light guide with high efficiency. Even in an illumination optical system in which a laser with a small Lagrangian invariant is used as a light source, the large size of the light source and the large divergence angle necessary at the time of the coupling to the light guide by the optical system can be compatible.

The illumination device, the illumination method, and the endoscope according to the first embodiment of the present disclosure have been described in detail above with reference to FIGS. 1 to 12C.

Second Embodiment

Hereinafter, an illumination device and an illumination method capable of reducing speckle noise of laser light emitted from light sources and an endoscope including the illumination device will be described in detail.

When a white light source is obtained, for example, laser light sources emitting red, green, and blue lasers are used. However, since a beam shape is different for each laser light source of each color (each wavelength), there is a difference in spatial coherence originating from the beam shape. Therefore, a phenomenon in which the size of speckle noise observed in each color (wavelength) differs occurs.

Accordingly, in light of the above-mentioned circumstance, an illumination device, an illumination method, and an endoscope capable of equalizing the size of speckle noise observed in each color (wavelength) to reduce the speckle noise according to a simpler method will be proposed below.

Configuration of Illumination Device

First, the configuration of the illumination device according to a second embodiment of the present disclosure will be described with reference to FIGS. 13A to 19. FIGS. 13A to 17 and 19 are explanatory diagrams schematically illustrating the configuration of the illumination device according to the second embodiment of the present disclosure. FIGS. 18A and 18B are explanatory diagrams for describing a positional relation between a pupil position of a collector lens and laser light.

An illumination device 2 according to the embodiment includes at least a laser light source 200, an optical fiber 220, and a diffuser 240, as schematically illustrated in FIG. 13A. The illumination device 2 according to the embodiment preferably further includes a coupling optical system 210 between the laser light source 200 and the optical fiber 220 and preferably further includes a collimator 230 between the optical fiber 220 and the diffuser 240, as schematically illustrated in FIG. 13B.

At least one laser light source 200 is installed in the illumination device 2 and emits laser light with a predetermined wavelength. In the illumination device 2 according to the embodiment, various semiconductor lasers or solid-state lasers can be used as the laser light sources 200, and a combination of the lasers and a wavelength conversion mechanism can also be used. The wavelength of the laser light emitted from the laser light source 200 may be appropriately selected according to which object or phenomenon is observed in an illumination target. Examples of the wavelength include the visible light band of wavelengths from about 400 nm to about 700 nm or a nearinfrared band used for ICG (Indocyanine green) fluorescence imaging. When the laser light is used as excited light for fluorescence excitation, observed fluorescence may include autofluorescence of a part irradiated with the excited light or chemical agent fluorescence originating from various fluorescent reagents introduced into an irradiated part.

The coupling optical system 210 is an optical system that optically couples the laser light emitted from the laser light source 200 with the optical fiber 220 installed at the rear stage. The configuration of the coupling optical system 210 is not particularly limited. The coupling optical system 210 may be appropriately combined with various optical elements of the related art to optically couple the laser light with the optical fiber 220 and includes at least one condensing lens (collector lens) that optically couples the laser light with the optical fiber 220.

The coupling optical system 210 preferably further includes a collimating lens that allows the laser light emitted from the laser light source 200 to be substantially parallel (in other words, converts the laser light into substantially parallel light fluxes) between the laser light source 200 and the collector lens. Here, "substantially parallel" refers to a state in which a radiation angle of light radiated from the collimating lens is the minimum and is realized when the position of a focal distance of the collimating lens accords with a beam waist position of the laser light emitted from the laser light source 200.

When white illumination light is realized by combining the plurality of laser light sources 200 such as a red semiconductor laser, a green light-emitting semiconductor excitation solid-state laser, and a blue reaction laser, at least one dichroic mirror or dichroic prism is further installed in addition to the collector lens in the coupling optical system 210. A plurality of beams of laser light emitted from the plurality of laser light sources 200 are multiplexed by the dichroic mirror or the dichroic prism to generate white light. The multiplexed light is condensed by the collector lens to be coupled to the optical fiber 220.

Herein, in the illumination device 2 according to the embodiment, the laser light is incident on an inlet end surface of the optical fiber 220 in an oblique direction with respect to the normal line of the inlet end surface. More specifically, when a condensing angle or a radiation angle of the laser light (or the multiplexed light) is less than a numerical aperture (that is, an allowable angle of incidence) of the optical fiber 220, an angle is applied to the laser light within the range of the numerical aperture (allowable angle of incidence) of the optical fiber 220, and thus the laser light is incident in the oblique direction with respect to the normal line of the inlet end surface. More preferably, in the illumination device 2 according to the embodiment, an angle component on the inlet end surface of the laser light includes a normal line direction of the inlet end surface. Thus, it is possible to reduce the speckle noise of the laser light emitted from the laser light source 200. A method of causing the laser light to be incident on the optical fiber 220 will be described again in detail below.

The optical fiber 220 guides the laser light guided by the coupling optical system 210 to the diffuser 240 installed at the rear stage in FIG. 13A or the collimator 230 installed at the rear stage in FIG. 13B. The optical fiber 220 is not particularly limited, but a multimode optical fiber (for example, a step-index type multimode fiber) of the related art can be used. The core diameter of the optical fiber 220 is not particularly limited either. For example, an optical fiber with a core diameter of about 1 mm can be used.

In the optical fiber 220 according to the embodiment, the laser light is guided in the oblique direction with respect to the normal line of the inlet end surface so that an angle of incidence is as large as possible within the range of the allowable numerical aperture of the optical fiber. Therefore, the radiation angle of the laser light emitted from an emission end of the optical fiber 220 is greater than the condensing angle of the laser light on the inlet end surface.

When the angle of incidence component of the laser light incident on the optical fiber 220 does not include the normal line direction of the inlet end surface, a far-field pattern (intensity distribution) of the laser light emitted from the emission end of the optical fiber 220 becomes a doughnut form in which the amount of light in the vicinity of the central optical axis of the optical fiber is less than the amount of light of the peripheral portion. Conversely, when the angle of incidence component of the laser light incident on the optical fiber 220 includes the normal line direction of the inlet end surface, the far-field pattern becomes a solid form of which the amount of light in the vicinity of the central optical axis of the optical fiber is equal to that of the peripheral portion. Accordingly, the illumination device 2 according to the embodiment is more preferably configured such that the angle of incidence component of the laser light incident on the optical fiber 220 includes the normal line direction of the inlet end surface and the far-field pattern (intensity distribution) of the laser light emitted from the emission end of the optical fiber 220 becomes a solid form.

The collimator 230 is installed downstream from the exit end of the optical fiber 220 and causes the laser light emitted from the optical fiber 220 to be substantially parallel. By causing the laser light emitted from the optical fiber 220 to be substantially parallel through the collimator 230, a diffusion state of the laser light can be easily controlled by a diffusion angle of the diffuser 240 in the diffuser 240 installed at the rear stage. The configuration of the collimator 230 is not particularly limited, but optical elements of the related art may be appropriately combined so that an optical system of the related art is configured to convert the laser light into the parallel light flux.

The diffuser 240 is installed at the rear stage of the optical fiber 220 (at the rear stage of the collimator 230 when the collimator 230 is installed) and diffuses the laser light emitted from the optical fiber 220 or the collimator 230 to generate a secondary light source. That is, the emission end of the light in the diffuser 240 functions as the secondary light source.

Here, a divergence angle of the light emitted from the diffuser 240 is controlled by the diffusion angle of the diffuser 240, as described in the foregoing first embodiment.

In the embodiment, the diffusion angle of the diffuser 240 is not particularly limited, but may be appropriately decided according to a size of the illumination device 2 to be realized, characteristic values of the diffuser applicable to the illumination device 2, or the like.

The kind of specific diffuser 240 is not particularly limited, but a diffusion element of the related art can be used. Examples of the diffuser include a frost type obscure glass, an opal type diffusion plate using diffusion characteristics, for example, by diffusing an optical diffusion material into glass, a holographic diffusion plate, a diffusion plate such as a microlens array, and a bundle fiber in which a plurality of optical fibers are bundled. The holographic diffusion plate is particularly preferred since a holographic pattern is applied to a predetermined substrate and any angle is set as a diffusion angle of exited light. The microlens array can set any angle as the diffusion angle of exited light. The diffusion effect by the bundle fiber is restrictive. For the light incident at an angle theta with respect to the normal line of an inlet end surface, an emitted beam disperses in a conic shape with an angle, the angle theta, with respect to the normal line of an exit end surface.

The configuration of the illumination device 2 according to the embodiment has been described in detail above with reference to FIGS. 13A and 13B.

Specific Example of Illumination Device

Next, the configuration of the illumination device according to the embodiment will be described specifically with reference to FIGS. 14A to 19.

Case in which Number of Laser Light Sources is 1

First, a case in which one laser light source is used as the laser light source 200 will be described with reference to FIGS. 14A to 15 as an example.

The laser light emitted from one laser light source 200 is guided to a collimating lens CL installed as the coupling optical system 210 and becomes substantially parallel to be converted into a parallel light flux. The laser light converted into the parallel light flux is guided to a collector lens L. The collector lens L optically couples the incident parallel light flux to the optical fiber 220 of a multimode single core. Here, a central optical axis of the laser light source 200, the collimating lens CL, and the collector lens L on the inlet end surface of the optical fiber 220 is incident in an oblique direction with respect to the optical axis (in other words, the normal line of the inlet end surface of the optical fiber 220) of the optical fiber 220. The magnitude of an angle formed between the two optical axes is theta. By causing the laser light to be incident on the inlet end surface of the optical fiber 220 in the oblique direction, it is possible to reduce speckle noise originating from the laser light source 200.

Further, when $\theta_{beam}$ is a condensing angle of the laser light on the inlet end surface of the optical fiber 220, as illustrated in FIG. 14B, and $\theta_{fiber}$ is an allowable angle of incidence of the optical fiber 220, as illustrated in FIG. 14C, a relation expressed by Expressions 201 and 201-2 below is preferably satisfied to reduce the speckling in the illumination device 2 according to the embodiment. Here, $\theta_{beam}$ is assumed to be less than $\theta_{fiber}$ in the expressions.

[Math. 10]

$$(\theta+\theta_{beam}) \leq \theta_{fiber} \qquad \text{(Expression 201)}$$

$$\theta \leq \theta_{beam} \qquad \text{(Expression 201-2)}$$

When the relation expressed by Expression 201 above is satisfied, the laser light propagates through the optical fiber 220 without loss. Further, when a larger theta is selected, the radiation angle of the laser light emitted from the optical fiber 220 further increases.

When the relation expressed by Expression 201-2 above is satisfied, an angle component of the laser light incident on the optical fiber 220 includes a normal line direction of the inlet end surface and the far-field pattern (intensity distribution) of the laser light emitted from the emission end of the optical fiber 220 becomes a solid form rather than a doughnut form.

In Expression 201 above, $(\theta+\theta_{beam})$ is more preferably equal to $\theta_{fiber}$. In this case, theta is the largest value and the largest radiation angle corresponding to the allowable angle of incidence of the optical fiber 220 can be obtained. When a relation beam) expressed by $(\theta+\theta_{beam})$ equal to $\theta_{fiber}$ is realized simultaneously with Expression 201-2, the laser light emitted from the optical fiber 220 has the largest radiation angle and the far-field pattern (intensity distribution) of the solid form.

The laser light guided to the optical fiber 220 is emitted from the exit end of the optical fiber 220 to be guided to the diffuser 240. In the diffuser 240, the beam from the optical fiber 220 is projected to form a secondary light source on a diffusion surface (an exit end surface of the diffuser 240) on the diffuser 240. The intensity distribution (or a beam size) on the diffusion surface of the second light source is the same as the intensity distribution (or a beam size) formed on the diffusion surface by the light from the optical fiber 220. The light from the secondary light source is radiated to an observation field so that an illumination target is illuminated with the light. When the illumination device 2 is used as a light source for an endoscope, the radiation angle of the secondary light source is set to be large to obtain a high viewing angle in many cases, and thus a diffuser with a large diffusion angle is selected.

The speckling observed in an illumination target decreases as the beam size of the secondary light source is larger and the far-field pattern becomes the solid form (uniform intensity distribution). Accordingly, by satisfying Expression 201 above and selecting a larger theta, it is possible to further reduce the speckle noise. Further, by satisfying the relation expressed by Expression 201-2 above, it is possible to further reduce the speckle noise.

In the illumination device 2 according to the embodiment, as in FIGS. 14A to 14C, the case in which the central optical axis of the laser light source 200, the collimating lens CL, and the collector lens L mutually and the optical axis of the optical fiber 220 intersect each other is illustrated. As illustrated in FIG. 15, however, a central axis of the parallel light flux of the laser light may be incident on the collector lens L in parallel to an optical axis formed by the collector lens L and the optical fiber 220 and at a deviated position of the optical axis.

In this case, as illustrated in FIG. 15, when $W_A$ is a beam width of the parallel light flux, f is a focal distance of the collector lens L, theta$_{fiber}$ is an allowable angle of incidence of the optical fiber 220, and D$_A$ is a shift amount from the center of the optical axis formed by the collector lens L and the optical fiber 220, relations expressed by Expressions 202 and 202-2 below are established. Then, it is preferable to reduce the speckling. Here, (W$_A$/2) is assumed to be less than (f×sin(theta$_{fiber}$)) in the expression.

[Math. 11]

$$(W_A/2)+D_A \leq (f \times \sin(\theta_{fiber})) \quad \text{(Expression 202)}$$

$$D_A \leq (W_A/2) \quad \text{(Expression 202-2)}$$

When the relation expressed by Expression 202 above is satisfied, the laser light propagates through the optical fiber 220 without loss. Further, when a larger D$_A$ is selected, the radiation angle of the laser light emitted from the optical fiber 220 further increases.

When the relation expressed by Expression 202-2 above is satisfied, an angle component of the laser light incident on the optical fiber 220 includes a normal line direction of the inlet end surface and the far-field pattern (intensity distribution) of the laser light emitted from the emission end of the optical fiber 220 becomes a solid form rather than a doughnut form.

In Expression 202 above, (W$_A$/2)+D$_A$ is more preferably equal to (f×sin(theta$_{fiber}$)). In this case, the largest radiation angle corresponding to the allowable angle of incidence of the optical fiber 220 can be obtained. When a relation expressed by (W$_A$/2)+D$_A$=(f×sin(theta$_{fiber}$)) realized simultaneously with Expression 202-2, the laser light is emitted from the optical fiber 220 has the largest radiation angle and the far-field pattern (intensity distribution) of the solid form.

The laser light guided to the optical fiber 220 is emitted from the exit end of the optical fiber 220 to be guided to the diffuser 240. In the diffuser 240, a beam from the optical fiber 220 is projected to form a secondary light source on a diffusion surface (an exit end surface of the diffuser 240) on the diffuser 240. The intensity distribution (or a beam size) on the diffusion surface of the secondary light source is the same as the intensity distribution (or a beam size) formed on the diffusion surface by the light from the optical fiber 220. The light from the secondary light source is radiated to an observation field so that an illumination target is illuminated with the light. When the illumination device 2 is used as a light source for an endoscope, the radiation angle of the secondary light source is set to be large to obtain a high viewing angle in many cases, and thus a diffuser with a large diffusion angle is selected.

The speckling observed in an illumination target decreases as the beam size of the secondary light source is larger and the far-field pattern becomes the solid form (uniform intensity distribution). Accordingly, by satisfying Expression 202 above and selecting a larger D$_A$, it is possible to further reduce the speckle noise. Further, by satisfying the relation expressed by Expression 202-2 above, it is possible to further reduce the speckle noise.

As illustrated in FIG. 16, a collimating lens (that is, a collimator) 230 may be disposed between the optical fiber 220 and the diffuser 240. FIG. 16 illustrates a case in which the central axis of the parallel light flux of the laser light is incident on the collector lens L in parallel to the optical axis formed by the collector lens L and the optical fiber 220 and at a deviated position of the optical axis. However, even when the laser light is incident on the inlet end surface of the optical fiber 220 in an oblique direction, the collimator 230 may, of course, be disposed in the same way.

Case in which Plurality of Laser Light Sources are Present

Next, a case in which a plurality of laser light sources are used as the laser light sources 200 will be described with reference to FIGS. 17 to 19 as an example.

Hereinafter, a case in which white light is realized using a red laser light source (Red) emitting red laser light, a green laser light source (Green), and a blue laser light source (Blue) will be described.

The red laser light emitted from the red laser light source is converted into a parallel light flux by a collimating lens CL, is subsequently reflected by a mirror M, and is guided to a collector lens L while being transmitted through two dichroic mirrors DM, as illustrated in FIG. 17.

Green laser light emitted from the green laser light source is converted into a parallel light flux by a collimating lens CL, is subsequently reflected by the dichroic mirror DM, and is guided to the collector lens L while being transmitted through the dichroic mirror DM for blue laser light.

The blue laser light emitted from the blue laser light source is converted into a parallel light flux by a collimating lens CL, is subsequently reflected by the dichroic mirror DM, and is guided to the collector lens L.

Further, as illustrated in FIG. 17, C1 is assumed to be the optical axis of the red laser light, C2 is assumed to be the optical axis of the green laser light, and C3 is assumed to be the optical axis of the blue laser light. The optical axis C1 of the red laser light is arranged to be the same as an optical axis C0 of the mirror M, the dichroic mirrors DM, the collector lens L, and the optical fiber 220.

FIG. 18A illustrates a beam disposition example on a cross-sectional surface A-A of FIG. 17. In FIG. 18A, a beam cross-sectional shape of the laser light source 200 (primary light source) is a perfect circle. Here, a beam with the largest beam width is arranged to accord with a beam central axis C1 and the central optical axis C0. In FIG. 18A, the beam with the largest beam width is the red beam and W1 is assumed to be the largest beam width. That is, in FIG. 18A, the beam widths of the laser light satisfy W1>W2 and W1>W3.

In FIG. 18A, the beam width of the red beam is selected in a range transmitting through the collector lens L and the optical fiber 220 at the rear stage. That is, when W0 is assumed to be an allowable transmission beam width decided in the collector lens L and the optical fiber 220, a relation of W0>W1 is satisfied.

In FIG. 18A, an allowable beam width is indicated by W0 and a beam (laser light) travelling inside an allowable outer circumference circle with a radius R0 shaped with the beam width W0 can be transmitted through the optical fiber 220. The shape of the allowable outer circumference circle is a shape decided by the collector lens L and the optical fiber 220. When a normal lens which is rotationally symmetric about an optical axis center C0 is used as the collector lens L, W0 has a perfect circle shape with the radius R0=W0/2.

Here, as illustrated in FIGS. 17 and 18A, beam central positions (that is, C2 and C3) of green and blue primary light source beams with widths narrower than the largest beam width do not accord with C0. The green and blue primary light source beams are disposed at positions moved in parallel to the central optical axis C0.

A range of the parallel movement of the green and blue primary light source beams is set such that the green and blue primary light source beams are located inside a circle (largest outer circumference circle of the beam) indicated with the largest radius (R1=W1/2 in FIG. 18A) shaped by the red primary light source beam. That is, when D2 is a distance of the parallel movement of the green primary light source beam from the central optical axis C0, the range of D2 is a range of greater than 0 and less than or equal to (R1−W2/2). When D3 is a distance of the parallel movement of the blue primary light source beam, the range of D3 is a range of greater than 0 and less than or equal to (R1−W3/2).

Here, in the illumination device 2 according to the embodiment, the remaining beams (at points P and Q in FIG. 18A) are preferably inscribed in the circle (largest outer circumference circle of the beam) which is shaped by the largest beam width and has the largest radius centering on C0 on a cross-sectional surface with respect to the optical axis, as illustrated in FIG. 18A.

In the example illustrated in FIG. 17A, the green and blue primary light source beams are preferably arranged to be inscribed in the largest outer circumference circle of the beam indicated by R1. That is, the distance D2 of the parallel movement of the green primary light source beam is D2=(R1−W2/2) and the distance D3 of the parallel movement of the blue primary light source beam is D3=(R1−W3/2).

In FIG. 18A, the green and blue primary light source beams with the narrow beam widths may preferably be disposed so that the green and blue primary light source beams are present in the range extending from the radius R0 to the radius R1 and centering on C0. That is, each of the red, green, and blue primary light source beams contains the optical axis center C0 in relations of W2 being greater than or equal to (W1/2) and W3 being greater than or equal to (W1/2).

This is because luminance at the central position is prevented from deteriorating in a far-sight image (that is, in an optical intensity distribution of the diffuser 240 of the optical system in FIG. 17) of the light radiated from an output end of the optical fiber 220 and a solid form is realized.

The laser light guided by the optical fiber 220 is emitted from the exit end of the optical fiber 220 to be guided to the diffuser 240. In the diffuser 240, the beam from the optical fiber 220 is projected to form a secondary light source on a diffusion surface (an exit end surface of the diffuser 240) on the diffuser 240. The intensity distribution (or a beam size) on the diffusion surface of the second light source is the same as the intensity distribution (or a beam size) formed on the diffusion surface by the light from the optical fiber 220.

Through the above-described operation, the red, green, and blue primary light source beams have substantially the same intensity distribution (or beam size) on the diffusion surface in the secondary light source. Therefore, the magnitude of the speckle noise observed in the illumination target with each color (wavelength) can be almost equal.

FIG. 18B illustrates another beam disposition example on the cross-sectional surface A-A of FIG. 17. In the example illustrated in FIG. 18B, the cross-sectional shape of each primary light source beam is elliptical.

Even in the example illustrated in FIG. 18B, the beam central positions (that is, C2 and C3) of the green and blue primary light source beams with widths narrower than the largest beam width do not accord with C0. The green and blue primary light source beams are disposed at positions moved in parallel to the central optical axis C0.

Even in this case, a range of the parallel movement of the green and blue primary light source beams is arranged such that the green and blue primary light source beams are located inside the largest outer circumference circle of the beam indicated with the largest radius (R1=W1/2) shaped by the red primary light source beam and centering on C0. As illustrated in FIG. 17B, each primary light source beam is preferably disposed so that the green and blue primary light source beams are inscribed in the largest outer circumference circle centering on C0.

More preferably, the green and blue primary light source beams with the narrow beam widths may be disposed so that the green and blue primary light source beams are present in the range extending from the radius R0 to the radius R1 and centering on C0. That is, each of the red, green, and blue primary light source beams contains the optical axis center C0. This is because luminance at the central position is prevented from deteriorating in a far-sight image (that is, in an optical intensity distribution of the diffuser 240 of the optical system in FIG. 17) of the light radiated from an output end of the optical fiber 220 and a solid form is realized.

Through the above-described operation, the red, green, and blue primary light source beams have substantially the same intensity distribution (or beam size) on the diffusion surface in the secondary light source. Therefore, the magnitude of the speckle noise observed in the illumination target with each color (wavelength) can be almost equal.

The parallel movement of the beams illustrated in FIGS. 17 to 18B described above can be adjusted by moving the dichroic mirrors DM, as described in the first embodiment.

As illustrated in FIG. 19, the collimating lens (that is, the collimator) 230 may be disposed between the optical fiber 220 and the diffuser 240.

The configuration of the illumination device according to the embodiment has been described specifically above with reference to FIGS. 17 to 19.

Configuration of Endoscope

Next, the configuration of an endoscope 10 in which the illumination device 2 according to the embodiment is used as an illumination light source will be described in brief with reference to FIG. 20. FIG. 20 is an explanatory diagram schematically illustrating the configuration of an endoscope including the illumination device according to the embodiment.

By coupling the secondary light source emitted using the above-described illumination device 2 as a light source to a light guide 901 included in any endoscope unit 900, a photographed image with reduced speckle noise can be obtained. The illumination light guided to the light guide 901 from the secondary light source is guided to an endoscope body 903 by the light guide 901 to be guided to a distal end portion of the endoscope.

Here, the endoscope unit 900 on which the illumination device 2 is mounted is not particularly limited, but any endoscope unit can be used as long as the endoscope unit 900 includes the general light guide 901.

By extending the optical fiber 220 of the illumination device 2 up to the distal end portion of the endoscope and installing the diffuser 240, an observation field may be illuminated with the illumination light from the secondary light source.

The endoscope 10 including the illumination device 2 according to the embodiment has been described in brief above with reference to FIG. 20.

Verification Example

Hereinafter, referring to FIGS. 21 to 24, an example in which the reduction degree of speckle noise is specifically verified will be described in a case in which the speckle noise is reduced by moving the axis of the laser light source 200 (the primary light source) in parallel from the optical axis.

In an example illustrated in FIG. 21, a semiconductor excitation solid-state laser for green emission was used as the laser light source 200. This laser is a laser light source radiating a collimated beam. In FIG. 21, a primary light source beam with a beam width of 1 mm was formed by using a slit with a width of 1 mm. The primary light source beam was condensed on the inlet end surface of the optical fiber 220 by using a step-index type multimode fiber with a core diameter of 1 mm as the optical fiber 220 and a collector lens L with a focal distance of 30 mm.

The secondary light source illuminating an illumination field was formed by placing a holographic diffusion plate as the diffuser 240 at a position 5 mm from the exit end surface of the optical fiber 220. The speckling was measured by placing a test chart at a position 300 mm from the position of the secondary light source and imaging the test chart with a CCD camera.

In the example illustrated in FIG. 21, an amount of speckling was measured at each movement position by moving the dichroic mirrors DM in an optical axis direction to move the optical axis center of the light incident on the collector lens L. An obtained measurement result is illustrated in FIG. 22. The horizontal axis of FIG. 22 represents a deviation amount from the central optical axis C0 of the optical fiber 220 and the vertical axis of FIG. 22 represents a speckle contrast ratio (SCR) corresponding to the amount of speckling.

As is apparent from the result illustrated in FIG. 22, it can be understood that the amount of speckling decreases as the shift amount increases.

In an example illustrated in FIG. 23, a bundle fiber was used as the diffuser 240. Further, a semiconductor excitation solid-state laser for green emission radiating a collimated beam was used as the laser light source 200. This laser is a laser light source radiating a collimated beam. In the example illustrated in FIG. 23, a primary light source beam with a beam width of 1 mm was formed by using a slit with a width of 1 mm. The primary light source beam was condensed on the inlet end surface of the optical fiber 220 by using a step-index type multimode fiber with a core diameter of 1 mm as the optical fiber 220 and a collector lens L with a focal distance of 30 mm.

The secondary light source illuminating an illumination field was formed on an exit end surface of the bundle fiber by placing the bundle fiber with a bundle diameter of 5 mm as the diffuser 240 at a position 10 mm from the exit end surface of the optical fiber 220. The speckling was measured by placing a test chart at a position 300 mm from the position of the secondary light source and imaging the test chart with a CCD camera.

In the example illustrated in FIG. 23, an amount of speckling was measured at each movement position by moving the dichroic mirrors DM in an optical axis direction to move the optical axis center of the light incident on the collector lens L. An obtained measurement result is illustrated in FIG. 24. The horizontal axis of FIG. 24 represents a deviation amount from the central optical axis C0 of the optical fiber 220 and the vertical axis of FIG. 24 represents a speckle contrast ratio (SCR) corresponding to the amount of speckling.

As is apparent from the result illustrated in FIG. 24, it can be understood that the amount of speckling decreases as the shift amount increases.

Third Embodiment

Hereinafter, a combination example of the method of reducing the speckle noise of the entire illumination device, as described in the first embodiment, and the method of reducing the speckle noise of the laser light emitted from the light sources, as described in the second embodiment, will be described in brief according to a third embodiment.

Configuration of Illumination Device

First, the configuration of the illumination device according to the third embodiment of the present disclosure will be described with reference to FIG. 25. FIG. 25 is an explanatory diagram schematically illustrating the configuration of the illumination device according to the embodiment.

As schematically illustrated in FIG. 25, an illumination device 3 according to the embodiment includes a laser light source 300, a coupling optical system 310, an optical fiber 320, a collimator 330, a diffuser 340, and a condenser 350.

At least one laser light source 300 is installed in the illumination device 3 and emits laser light with a predetermined wavelength. In the illumination device 3 according to the embodiment, various semiconductor lasers or solid-state lasers can be used as the laser light sources 300, and a combination of the lasers and a wavelength conversion mechanism can also be used. The wavelength of the laser light emitted from the laser light source 300 may be appropriately selected according to which object or phenomenon is observed in an illumination target. Examples of the wavelength include the visible light band of wavelengths from about 400 nm to about 700 nm or a nearinfrared band used for ICG (Indocyanine green) fluorescence imaging. When the laser light is assumed to be excited light for fluorescence excitation, observed fluorescence may include autofluorescence of a part irradiated with the excited light or chemical agent fluorescence originating from various fluorescent reagents introduced into an irradiated part.

The coupling optical system 310 is an optical system that optically couples the laser light emitted from the laser light source 300 with the optical fiber 320 installed at the rear stage. The configuration of the coupling optical system 310 is not particularly limited. The coupling optical system 310 may be appropriately combined with various optical elements of the related art to optically couple the laser light with the optical fiber 320 and includes at least one condensing lens (collector lens) that optically couples the laser light with the optical fiber 320.

When the plurality of laser light sources 300 are combined to realize white illumination light, at least one dichroic mirror or dichroic prism is further installed in addition to the collector lens in the coupling optical system 310. A plurality of beams of laser light emitted from the plurality of laser light sources 300 are multiplexed by the dichroic mirror or the dichroic prism to generate white light. The multiplexed light is condensed by the collector lens to be coupled to the optical fiber 320.

When the plurality of laser light sources 300 are used in combination, the numerical apertures on which the laser light is incident on the optical fiber 320 are preferably aligned. However, because the FFP of each laser differs, it is difficult to align the numerical apertures of incidence in practice. Accordingly, in this case, in the coupling optical system 310, a numerical aperture adjustment unit is installed using the same method described in the first and second embodiments.

The optical fiber 320 guides the laser light guided by the coupling optical system 310 to the collimator 330 installed at the rear stage. The light emitted from the optical fiber 320 becomes a rotationally symmetric beam, which contributes to uniformity of a luminance distribution. The optical fiber 320 is not particularly limited, but a multimode optical fiber (for example, a step-index type multimode fiber) of the related art can be used. The core diameter of the optical fiber 320 is not particularly limited either. For example, an optical fiber with a core diameter of about 1 mm can be used.

In the optical fiber 320 according to the embodiment, light is guided to an inlet end of the optical fiber 320 so that the numerical apertures between the plurality of light sources accord as much as possible at the inlet end of the optical fiber. At this time, for example, by optimizing a focal distance of a lens collimating the laser light emitted from the laser light sources, the laser light emitted from an emission end of the optical fiber 320 preferably becomes a solid beam for which the amount of light in the vicinity of the central optical axis of the optical fiber is equal to that of the peripheral portion of the optical fiber, rather than a beam with a doughnut form in which the amount of light in the vicinity of the central optical axis of the optical fiber is less than the amount of light of the peripheral portion.

The collimator 330 is installed downstream from the exit end of the optical fiber 320 and converts the laser light emitted from the optical fiber 320 into a parallel light flux. By converting the laser light into the parallel light flux by the collimator 330, a diffusion state of the laser light can be easily controlled by a diffusion angle of the diffuser 340 in the diffuser 340 installed at the rear stage. The configuration of the collimator 330 is not particularly limited, but optical elements of the related art may be appropriately combined so that an optical system of the related art is configured to convert the laser light into the parallel light flux.

The diffuser 340 is installed near a rear focal position of the collimator 330 and diffuses the parallel light flux emitted from the collimator 330 to generate a secondary light source. That is, the emission end of the light in the diffuser 340 functions as the secondary light source.

The size of the secondary light source generated by the diffuser 340 can be controlled by the focal distance of the collimator 330. NA of the exited light can be controlled by the diffusion angle of a diffusion plate. The Lagrangian invariant indicated by Expression 2 above can be enlarged by the effects of both of the constituents, and thus a desired light source size and a desired illumination range can be compatible.

When the size of the secondary light source is desired to be adjusted, the size of the secondary light source may be optimized by the exit NA from the optical fiber and the focal distance of the collimator.

The light emitted from the diffuser 340 is guided to the condenser 350. The condenser 350 forms an image of the secondary light source formed by the diffuser 340 to an illumination target at a predetermined paraxial lateral magnification. An example of the illumination target includes an inlet end of a light guide located downstream from the condenser 350 and installed in an endoscope unit. Here, the condenser 350 according to the embodiment is different from that of the related art and forms an image of the secondary light source so that the area of the illumination target (for example, the inlet end of the light guide installed in the endoscope unit) is filled as much as possible. Thus, the illumination device 3 can reduce the speckle noise as a whole.

An image formation magnification (paraxial lateral magnification) beta of the condenser 350 is expressed by Expression 102 above by a focal distance f of the condenser and a distance X between the focal position F and an object surface.

Further, in the illumination device 3 according to the embodiment, the size of an image of the secondary light source is preferably controlled so that a relation expressed by Expression 106 above is established when $phi_{LG}$ is the diameter of the inlet end of the light guide on which the secondary light source transmitted through the condenser 350 is incident and Y' is the size of the image of the secondary light source.

The paraxial lateral magnification beta of the condenser 350 may be decided appropriately so that the size Y' of the image of the secondary light source satisfies the range of Expression 106 above and more preferably satisfies greater than or equal to 0.4 and less than or equal to 2.3.

The configuration of the illumination device 3 according to the embodiment has been described in detail above with reference to FIG. 25.

Configuration of Endoscope

Next, the configuration of an endoscope 10 in which the illumination device 3 according to the embodiment is used as an illumination light source will be described in brief with reference to FIG. 26. FIG. 26 is an explanatory diagram schematically illustrating the configuration of an endoscope including the illumination device according to the embodiment.

The image of the light source by the condenser is formed in a light guide 901 included in any endoscope unit 900 by using the above-described illumination device 3 as a light source so that illumination light with reduced speckle noise can be obtained. The illumination light guided to the light guide 901 is guided to an endoscope body 903 by the light guide 901 to be guided to a distal end portion of the endoscope.

Here, the endoscope unit 900 on which the illumination device 3 is mounted is not particularly limited, but any endoscope unit can be used as long as the endoscope unit 900 includes the general light guide 901. In contrast, when the endoscope unit 900 including the specific light guide 901 is desired to be used, the size Y' of the image of the secondary light source of the illumination device 3 according to the embodiment or the paraxial lateral magnification beta of the condenser 350 may be set according to the allowable numerical aperture $NA_L$ of incidence of the light guide 901.

The endoscope 10 including the illumination device 3 according to the embodiment has been described in brief above with reference to FIG. 26.

It should be understood by those skilled in the art that various modifications, combinations, sub-combinations and alterations may occur depending on design requirements and other factors insofar as they are within the scope of the appended claims or the equivalents thereof.

For example, in addition to the technical spirits described in the foregoing third embodiment, the various technical spirits described in the first embodiment can be applied to the second embodiment and the various technical spirits described in the second embodiment can be applied to the second embodiment can also be applied to the first embodiment.

In addition, the effects described in the present specification are merely illustrative and demonstrative, and not limitative. In other words, the technology according to the present disclosure can exhibit other effects that are evident to those skilled in the art along with or instead of the effects based on the present specification.

Additionally, the present technology may also be configured as below.

(1)

An illumination device including:

at least one laser light source configured to emit laser light;

a coupling optical system configured to couple the laser light emitted from the laser light source to an optical fiber;

a collimating optical system configured to convert the laser light emitted from the optical fiber into a parallel light flux;

a diffusion member disposed near a rear side focal position of the collimating optical system and configured to generate a secondary light source by diffusing the parallel light flux; and a condenser optical system configured to form an image of the secondary light source at an inlet end of a light guide at a predetermined paraxial lateral magnification.

(2)

The illumination device according to (1), wherein a relation expressed by Expression 1 below is established when Y' is a size of the image of the secondary light source formed at the inlet end of the light guide by the condenser optical system and $\text{phi}_{LG}$ is a diameter of the inlet end of the light guide:

[Math. 12]

$$0.8 \leq Y'/\varphi_{LG} \leq 1.2 \quad \text{(Expression 1)}$$

(3)

The illumination device according to (1) or (2), wherein the paraxial lateral magnification of the condenser optical system is in a range of 0.4 to 2.3.

(4)

The illumination device according to (2) or (3), wherein a relation of $Y' = \text{phi}_{LG}$ is established when Y' is a size of the image of the secondary light source formed at the inlet end of the light guide by the condenser optical system and $\text{phi}_{LG}$ is a diameter of the inlet end of the light guide.

(5)

The illumination device according to any one of (1) to (4), wherein a plurality of the laser light sources are installed, and wherein the coupling optical system includes a numerical aperture adjustment unit configured to align numerical apertures of incidence on the optical fiber between beams of the laser light emitted from the laser light sources.

(6)

The illumination device according to (5), wherein the numerical aperture adjustment unit includes at least a dichroic mirror or a dichroic prism, and adjusts the numerical aperture of incidence according to a position on which the laser light is incident on the dichroic mirror or the dichroic prism or a disposition position of the dichroic mirror or the dichroic prism with respect to a central optical axis of the coupling optical system.

(7)

The illumination device according to any one of (1) to (6), wherein at least one of the beams of laser light transmitted through the coupling optical system is incident on an inlet end surface of the optical fiber in an oblique direction with respect to a normal line of the inlet end surface.

(8)

The illumination device according to any one of (1) to (7), wherein a plurality of the laser light sources are installed, wherein a relation expressed by Expression 1 below is established in at least one of the laser light sources when Y' is a size of the secondary light source formed at the inlet end of the light guide by the condenser optical system and $\text{phi}_{LG}$ is a diameter of the inlet end of the light guide:

[Math. 13]

$$0.8 \leq Y'/\varphi_{LG} \leq 1.2 \quad \text{(Expression 1), and}$$

wherein, in the laser light sources other than at least the one of the laser light sources, the coupling optical system includes a numerical aperture adjustment unit configured to align numerical apertures of incidence on the optical fiber between beams of the laser light emitted from the laser light sources.

(9)

The illumination device according to any one of (1) to (8), wherein the condenser optical system is formed by a lens system in which a surface on a side on which the secondary light source is formed is a plane and a surface on which the image of the secondary light source is formed is a plane.

(10)

The illumination device according to (9), wherein the condenser optical system is formed by a lens system including a positive plano-convex lens with a plane oriented toward the diffusion member, one or more positive lenses, and a positive plano-convex lens with a plane oriented toward a rear end of the condenser optical system in order from the side of the diffusion member.

(11)

The illumination device according to (9), wherein a surface of the plano-convex lens which is located closest to the side on which the secondary light source in the condenser optical system is formed on a side of the diffusion member is an aspheric surface.

(12)

The illumination device according to any one of (1) to (11), wherein the laser light source is at least one of a semiconductor laser and a solid-state laser.

(13)

The illumination device according to any one of (1) to (12), wherein the diffusion member is a holographic diffusion plate in which a holographic pattern is applied or a microlens array.

(14)

An illumination method including:

coupling laser light emitted by at least one laser light source to an optical fiber via a coupling optical system;

converting, by a collimating optical system, the laser light emitted from the optical fiber into a parallel light flux;

diffusing, by a diffusion member disposed near a rear side focal position of the collimating optical system, the parallel light flux to generate a secondary light source; and forming an image of the secondary light source at an inlet end of a light guide at a predetermined paraxial lateral magnification.

(15)

An endoscope including:

an illumination device including at least one laser light source that emits laser light, a coupling optical system that couples the laser light emitted from the laser light source to an optical fiber, a collimating optical system that converts the laser light emitted from the optical fiber into a parallel light flux, a diffusion member that is disposed near a rear side focal position of the collimating optical system and generates a secondary light source by diffusing the parallel light flux, and a condenser optical system that forms an image of the secondary light source at an inlet end of a light guide at a predetermined paraxial lateral magnification; and a light guide on which the laser light emitted from the illumination device is incident.

(16)

An illumination device including:

at least one laser light source configured to emit laser light;

an optical fiber on which the laser light emitted from the laser light source is incident; and a diffusion member configured to generate a secondary light source by diffusing the laser light emitted from the optical fiber, wherein the laser light is incident on an inlet end surface of the optical fiber in an oblique direction with respect to a normal line of the inlet end surface.

(17)
The illumination device according to (16), wherein the laser light is incident on the optical fiber via a coupling optical system including at least a condensing lens and is incident on the condensing lens in parallel to an optical axis formed by the condensing lens and the optical fiber and at a position deviated from a center of the optical axis.

(18)
The illumination device according to (16), wherein the laser light is incident on the optical fiber via a collimating lens converting the laser light into a parallel light flux and a coupling optical system including at least a condensing lens installed at a rear end of the collimating lens and is incident on the condensing lens in parallel to an optical axis formed by the condensing lens and the optical fiber and at a position deviated from a center of the optical axis.

(19)
The illumination device according to (18),
wherein a plurality of the laser light sources are installed, and
wherein at least the laser light for which a beam width of the parallel light flux is narrow is incident in parallel to the optical axis formed by the condensing lens and the optical fiber and at the position deviated from the center of the optical axis.

(20)
The illumination device according to any one of (16) to (19), wherein a collimating lens converting the laser light emitted from the optical fiber into a parallel light flux is disposed between the optical fiber and the diffusion member.

(21)
The illumination device according to any one of (16) to (20), wherein a relation expressed by Expression 2 below is established when $\theta_{fiber}$ is an allowable angle of incidence of the optical fiber, $\theta_{beam}$ is a condensing angle of the laser light on an inlet end surface of the optical fiber, and theta is an angle formed between an optical axis of the optical fiber on the inlet end surface of the optical fiber and a central optical axis of the laser light:

[Math. 14]

$$(\theta+\theta_{beam}) \leq \theta_{fiber} \qquad \text{(Expression 2)}.$$

(22)
The illumination device according to any one of (16) to (21), wherein a relation expressed by Expression 2-2 below is established when $\theta_{beam}$ is a condensing angle of the laser light on an inlet end surface of the optical fiber and theta is an angle formed between an optical axis of the optical fiber on the inlet end surface of the optical fiber and a central optical axis of the laser light:

[Math. 15]

$$\theta \leq \theta_{beam} \qquad \text{(Expression 2-2)}.$$

(23)
The illumination device according to any one of (18) to (20), wherein a relation expressed by Expression 3 below is established when $W_A$ is a beam width of the parallel light flux, f is a focal distance of the condensing lens, $\theta_{fiber}$ is an allowable angle of incidence of the optical fiber, and $D_A$ is a shift amount from the center of the optical axis:

[Math. 16]

$$(W_A/2)+D_A \leq (f \times \sin(\theta_{fiber})) \qquad \text{(Expression 3)}.$$

(24)
The illumination device according to any one of (18) to (20) and (23), wherein a relation expressed by Expression 3-2 below is established when $W_A$ is a beam width of the parallel light flux and $D_A$ is a shift amount from the center of the optical axis:

[Math. 17]

$$D_A \leq (W_A/2) \qquad \text{(Expression 3-2)}.$$

(25)
The illumination device according to any one of (19), (20), and (23), wherein, on a cross-sectional surface perpendicular to the optical axis, each of the parallel light fluxes is inscribed in one circle centering on the optical axis.

(26)
The illumination device according to any one of (19), (20), and (24), wherein, on a cross-sectional surface perpendicular to the optical axis, each of the parallel light fluxes contains the optical axis.

(27)
The illumination device according to any one of (19), (20), (25), and (26), wherein wavelengths of the laser light emitted from the plurality of laser light sources form at least white light.

(28)
The illumination device according to any one of (16) to (27), wherein the diffusion member is a diffusion plate or a bundle fiber.

(29)
The illumination device according to any one of (16) to (28), wherein the laser light source is one of a semiconductor laser and a solid-state laser.

(30)
An illumination method including:
guiding laser light emitted from at least one laser light source to an optical fiber; and
generating, by a diffusion element, a secondary light source by diffusing the laser light emitted from the optical fiber,
wherein the laser light is incident on an inlet end surface of the optical fiber in an oblique direction with respect to a normal line of the inlet end surface.

(31)
An endoscope including:
an illumination device including at least one laser light source configured to emit laser light, an optical fiber on which the laser light emitted from the laser light source is incident, and a diffusion element configured to generate a secondary light source by diffusing the laser light emitted from the optical fiber,
wherein the laser light is incident on an inlet end surface of the optical fiber in an oblique direction with respect to a normal line of the inlet end surface.

(32)
An illumination apparatus, comprising:
an optical apparatus configured to optically process laser light to produce illumination light, the optical apparatus comprising:
at least one collimator configured to collimate the laser light; and
a diffuser configured to diffuse the laser light.

(33)
The illumination apparatus of (32), wherein the optical apparatus further comprises: an optical fiber; and
at least one collector configured to provide the laser light to the optical fiber.
(34)
The illumination apparatus of (33), wherein the diffuser is configured to receive the laser light from the optical fiber, either directly or indirectly.
(35)
The illumination apparatus of any one of (32) to (34), further comprising:
a plurality of laser light sources including:
a first laser light source configured to emit first laser light of a first wavelength; and
a second laser light source configured to emit second laser light of a second wavelength,
wherein the optical apparatus is configured to combine the first laser light and the second laser light to produce the illumination light.
(36)
The illumination apparatus of (35), wherein the plurality of laser light sources further includes a third laser light source configured to emit third laser light of a third wavelength, wherein the optical apparatus is configured to combine the first laser light, the second laser light and the third laser light to produce the illumination light, wherein the illumination light comprises white light.
(37)
The illumination apparatus of any one of (32) to (36), wherein the optical apparatus is configured to process the laser light such that speckle noise in the illumination light is reduced.
(38)
The illumination apparatus of any one of (32) to (37), further comprising a condenser configured to receive the laser light.
(39)
The illumination apparatus of (38), wherein the condenser is configured to receive the light from the diffuser.
(40)
The illumination apparatus of (38) or (39), wherein the condenser is configured to provide the laser light to a light guide.
(41)
The illumination apparatus of (32), wherein the optical apparatus further comprises: an optical fiber;
at least one collector configured to provide the laser light to the optical fiber; and a condenser;
wherein the at least one collimator is configured to receive the laser light from the optical fiber.
(42)
The illumination apparatus of (41), wherein the condenser is configured to provide the laser light to a light guide.
(43)
The illumination apparatus of (32), wherein the optical apparatus further comprises: an optical fiber; and
at least one collector configured to receive the laser light from the at least one collimator and provide the laser light to the optical fiber,
wherein the diffuser is configured to receive the laser light from the optical fiber.
(44)
The illumination apparatus of (43), wherein the optical fiber is configured to receive the laser light at an oblique angle with respect to a normal line of an inlet end surface of the optical fiber.
(45)
The illumination apparatus of (44), wherein the at least one collimator comprises a collimating lens, and wherein a central axis of parallel light flux from the collimating lens is aligned with an optical axis of the at least one collector.
(46)
The illumination apparatus of any one of (42), wherein the at least one collimator comprises at least one collimating lens, and wherein a central axis of parallel light flux from the at least one collimating lens is shifted in position with respect to an optical axis of the at least one collector.
(47)
The illumination apparatus of (46), wherein the at least one collimating lens comprises a first collimating lens configured to collimate first laser light of a first wavelength and a second collimating lens configured to collimate second laser light of a second wavelength, wherein, at a position where the first and second laser light from the first and second collimating lenses reaches the at least one collector, a central axis of parallel light flux from the first collimating lens is shifted in position with respect to a central axis of parallel light flux from the second collimating lens.
(48)
The illumination apparatus of (32), wherein the at least one collimator is at least one first collimator, and the illumination apparatus further comprises:
an optical fiber;
at least one collector configured to provide the laser light to the optical fiber; and
at least one second collimator configured to receive the laser light from the optical fiber,
wherein the at least one first collimator comprises a first collimating lens configured to collimate first laser light of a first wavelength and a second collimating lens configured to collimate second laser light of a second wavelength,
wherein, at a position where the first and second laser light from the first and second collimating lenses reaches the at least one collector, a central axis of parallel light flux from the first collimating lens is shifted in position with respect to a central axis of parallel light flux from the second collimating lens,
wherein the diffuser is configured to receive the laser light from the at least one second collimator.
(49)
A medical imaging system, comprising:
at least one laser light source configured to emit laser light;
an illumination apparatus, including:
an optical apparatus configured to optically process the laser light to produce illumination light, the optical apparatus comprising:
at least one collimator configured to collimate the laser light; and
a diffuser configured to diffuse the laser light; and
a medical imaging device configured to receive the illumination light.
(50)
The medical imaging system of (49), wherein the medical imaging device is an endoscope.
(51)
An illumination method, comprising:
optically processing laser light to produce illumination light, at least in part by:
A) collimating the laser light; and
B) diffusing the laser light.

REFERENCE SIGNS LIST 1, 2, 3 illumination device
100, 200, 300 laser light source 110, 210, 310 coupling optical system
120, 220, 320 optical fiber
130, 230, 330 collimator
140, 240, 340 diffuser
150, 250, 350 condenser

The invention claimed is:

1. An illumination system, comprising:
an optical apparatus configured to optically process laser light to produce illumination light, the optical apparatus comprising:
at least one collimator configured to collimate the laser light; and
a diffuser configured to diffuse the laser light,
wherein the at least one collimator is at least one first collimator, and the illumination system further comprises:
a first light guide;
at least one collector configured to provide the laser light to the first light guide; and
at least one second collimator configured to receive the laser light from the first light guide,
wherein the at least one first collimator comprises a first collimating lens configured to collimate first laser light of a first wavelength and a second collimating lens configured to collimate second laser light of a second wavelength,
wherein, at a position where the first and second laser light from the first and second collimating lenses reaches the at least one collector, a central axis of parallel light flux from the first collimating lens is shifted in position with respect to a central axis of parallel light flux from the second collimating lens,
wherein the diffuser is configured to receive the laser light from the at least one second collimator.

2. The illumination system of claim 1, wherein the first light guide includes an optical fiber.

3. The illumination system of claim 1, wherein the diffuser is configured to receive the laser light from the first light guide, either directly or indirectly.

4. The illumination system of claim 1, further comprising:
a plurality of laser light sources including:
a first laser light source configured to emit first laser light of a first wavelength; and
a second laser light source configured to emit second laser light of a second wavelength,
wherein the optical apparatus is configured to combine the first laser light and the second laser light to produce the illumination light.

5. The illumination system of claim 4, wherein the plurality of laser light sources further includes a third laser light source configured to emit third laser light of a third wavelength, wherein the optical apparatus is configured to combine the first laser light, the second laser light and the third laser light to produce the illumination light, wherein the illumination light comprises white light.

6. The illumination system of claim 1, wherein the optical apparatus is configured to process the laser light such that speckle noise in the illumination light is reduced.

7. The illumination system of claim 1, further comprising a condenser configured to receive the laser light.

8. The illumination system of claim 7, wherein the condenser is configured to receive the light from the diffuser.

9. The illumination system of claim 7, wherein the condenser is configured to provide the laser light to a second light guide.

10. The illumination system of claim 9, wherein the second light guide is configured to guide the laser light to a medical observation system and illuminate a target object as the illumination light.

11. The illumination system of claim 10, wherein the medical observation system includes at least one of a microscopic system or an endoscopic system.

12. The illumination system of claim 1, wherein a wavelength band of the laser light includes a visible light band or a near infrared band.

13. The illumination system of claim 1, wherein the first light guide is configured to receive the laser light at an oblique angle with respect to a normal line of an inlet end surface of the first light guide.

14. The illumination system of claim 13, wherein the laser light includes a light of a normal direction of an incident end face of the first light guide.

15. The illumination system of claim 13, wherein a condenser is configured to form an image of a secondary light source at an inlet end of a second light guide at a predetermined paraxial lateral magnification.

16. The illumination system of claim 15, wherein a relation expressed by Expression 1 below is established when Y' is a size of the image of the secondary light source formed at the inlet end of the second light guide by a condenser optical system and phi LG is a diameter of the inlet end of the second light guide:

$$0.8 \leq Y'/\varphi_{LG} \leq 1.2. \quad \text{(Expression 1)}$$

17. The illumination system of claim 16, wherein a relation of Y'=phi LG is established when Y' is a size of the image of the secondary light source formed at the inlet end of the second light guide by the condenser optical system and phi LG is a diameter of the inlet end of the second light guide.

18. The illumination system of claim 15, comprising a plurality of laser light sources, wherein a relation expressed by Expression 1 below is established in at least one of the plurality of laser light sources when Y' is a size of the secondary light source formed at the inlet end of the second light guide by a condenser optical system and phi LG is a diameter of the inlet end of the second light guide:

$$0.8 \leq Y'/\varphi_{LG} \leq 1.2. \quad \text{(Expression 1)}$$

wherein, in the plurality of laser light sources, a coupling optical system includes a numerical aperture adjustment unit configured to align numerical apertures of incidence on the first light guide between beams of the laser light emitted from the plurality of laser light sources.

19. The illumination system of claim 13, wherein an end portion of a laser light having a largest beam diameter and an end portion of a laser light other than the laser light having the largest beam diameter comes into contact with each other.

20. The illumination system of claim 15, wherein the predetermined paraxial lateral magnification of a condenser optical system is in a range of 0.4 to 2.3.

21. The illumination system of claim 15, wherein a condenser optical system is formed by a lens system in which a surface on a side on which the secondary light source is formed is a plane and a surface on which the image of the secondary light source is formed is a plane.

22. The illumination system of claim 21, wherein a condenser optical system is formed by a lens system including a positive plano-convex lens with a plane oriented toward a diffuser, one or more positive lenses, and a positive plano-convex lens with a plane oriented toward a rear end of the condenser optical system in order from the side of the diffuser.

23. The illumination system of claim 22, wherein a surface of the positive plano-convex lens which is located closest to the side on which the secondary light source in the condenser optical system is formed on a side of the diffuser is an aspheric surface.

24. The illumination system of claim 1 comprising a plurality of laser light sources, and wherein a coupling optical system includes a numerical aperture adjustment unit configured to align numerical apertures of incidence on the first light guide between beams of the laser light emitted from the plurality of laser light sources.

25. The illumination system of claim 24, wherein the numerical aperture adjustment unit includes at least a dichroic mirror or a dichroic prism, and adjusts a numerical aperture of incidence according to a position on which the laser light is incident on the dichroic mirror or the dichroic prism or a disposition position of the dichroic mirror or the dichroic prism with respect to a central optical axis of the coupling optical system.

26. The illumination system of claim 1, wherein at least one beam of the laser light is incident on an inlet end surface of the first light guide in an oblique direction with respect to a normal line of the inlet end surface.

27. The illumination system of claim 1, wherein a source of the laser light is at least one of a semiconductor laser and a solid-state laser.

28. The illumination system of claim 1, wherein the diffuser is a holographic diffusion plate in which a holographic pattern is applied or a microlens.

29. An illumination method, comprising:
with an optical apparatus of an illumination system, optically processing laser light to produce illumination light, the optical apparatus comprising:
at least one collimator configured to collimate the laser light; and
a diffuser configured to diffuse the laser light,
wherein the at least one collimator is at least one first collimator, and the illumination system further comprises:
a first light guide;
at least one collector that provides the laser light to the first light guide; and
at least one second collimator that receives the laser light from the first light guide,
wherein the at least one first collimator comprises a first collimating lens that collimates first laser light of a first wavelength and a second collimating lens that collimates second laser light of a second wavelength,
wherein, at a position where the first and second laser light from the first and second collimating lenses reaches the at least one collector, a central axis of parallel light flux from the first collimating lens is shifted in position with respect to a central axis of parallel light flux from the second collimating lens,
wherein the diffuser is receives the laser light from the at least one second collimator.

* * * * *